(12) United States Patent
Chen et al.

(10) Patent No.: US 10,105,357 B2
(45) Date of Patent: Oct. 23, 2018

(54) INDICATION OF ANTIBIOTIC DRUGS FOR PREPARATION OF CANCER INHIBITION PHARMACEUTICAL COMPOSITION

(71) Applicant: LAUNX BIOMEDICAL CO., LTD., Kaohsiung (TW)

(72) Inventors: Chiu-Hung Chen, Kaohsiung (TW); Show-Mei Chuang, Taichung (TW); Nai-Wan Hsiao, Taichung (TW); Ruei-Yue Liang, Taichung (TW); Xiao-Tong Tan, Taichung (TW)

(73) Assignee: LAUNX BIOMEDICAL CO., LTD., Kaohsiung (TW)

( * ) Notice: Subject to any disclaimer, the term of this patent is extended or adjusted under 35 U.S.C. 154(b) by 0 days.

(21) Appl. No.: 15/521,517

(22) PCT Filed: Oct. 23, 2015

(86) PCT No.: PCT/CN2015/092686
§ 371 (c)(1),
(2) Date: Apr. 24, 2017

(87) PCT Pub. No.: WO2016/062271
PCT Pub. Date: Apr. 28, 2016

(65) Prior Publication Data
US 2017/0304387 A1 Oct. 26, 2017

Related U.S. Application Data

(60) Provisional application No. 62/068,298, filed on Oct. 24, 2014.

(51) Int. Cl.
| | |
|---|---|
| A61K 31/505 | (2006.01) |
| A61K 31/4427 | (2006.01) |
| A61K 31/085 | (2006.01) |
| A61K 31/137 | (2006.01) |
| C07C 211/27 | (2006.01) |
| C07C 211/30 | (2006.01) |
| A61K 38/02 | (2006.01) |
| A61K 38/14 | (2006.01) |
| A61K 31/4525 | (2006.01) |
| A61K 31/138 | (2006.01) |
| A61K 31/196 | (2006.01) |
| A61K 31/197 | (2006.01) |
| A61K 31/216 | (2006.01) |
| A61K 31/341 | (2006.01) |
| A61K 31/366 | (2006.01) |
| A61K 31/404 | (2006.01) |
| A61K 31/549 | (2006.01) |
| A61K 31/55 | (2006.01) |
| A61K 31/7056 | (2006.01) |
| A61K 38/05 | (2006.01) |
| A61K 45/06 | (2006.01) |
| A61K 31/381 | (2006.01) |
| A61K 31/00 | (2006.01) |
| A61K 38/00 | (2006.01) |

(52) U.S. Cl.
CPC ........ *A61K 31/4427* (2013.01); *A61K 31/085* (2013.01); *A61K 31/137* (2013.01); *A61K 31/138* (2013.01); *A61K 31/196* (2013.01); *A61K 31/197* (2013.01); *A61K 31/216* (2013.01); *A61K 31/341* (2013.01); *A61K 31/366* (2013.01); *A61K 31/381* (2013.01); *A61K 31/404* (2013.01); *A61K 31/4525* (2013.01); *A61K 31/505* (2013.01); *A61K 31/549* (2013.01); *A61K 31/55* (2013.01); *A61K 31/7056* (2013.01); *A61K 38/02* (2013.01); *A61K 38/05* (2013.01); *A61K 38/14* (2013.01); *A61K 45/06* (2013.01); *C07C 211/27* (2013.01); *C07C 211/30* (2013.01); *A61K 31/00* (2013.01); *A61K 38/00* (2013.01); *A61K 2300/00* (2013.01)

(58) Field of Classification Search
CPC .............................. A61K 31/505; A61K 31/05
USPC .......................................... 514/272, 733, 275
See application file for complete search history.

(56) References Cited

U.S. PATENT DOCUMENTS

2009/0054312 A1* 2/2009 Wolf .................. G01N 33/5011
514/1.1

FOREIGN PATENT DOCUMENTS

CN 102688493 A * 9/2012

* cited by examiner

*Primary Examiner* — Shengjun Wang
(74) *Attorney, Agent, or Firm* — Liang Legal Group, PLLC

(57) ABSTRACT

A method for treating a cancer includes administering to a subject in need thereof a pharmaceutical composition containing a therapeutically effective amount of an antibiotic drug or a pharmaceutical acceptable salt thereof. The antibiotic drug is selected from the group consisting of an aminoglycoside antibiotic drug, an anti-fungal antibiotic drug, a Cephalosporin antibiotic drug, a β-propionamide antibiotic drug, a chloramphenicol antibiotic drug, an erythromycin antibiotic drug, a penicillin antibiotic drug, and a tetracycline antibiotic drug.. The cancer is selected from the group consisting of lung cancer, gastrointestinal tract cancer, colorectal cancer, prostate cancer, bladder cancer, cervical cancer, breast cancer, and blood cancer.

1 Claim, 1 Drawing Sheet

INDICATION OF ANTIBIOTIC DRUGS FOR PREPARATION OF CANCER INHIBITION PHARMACEUTICAL COMPOSITION

CROSS-REFERENCE TO RELATED APPLICATIONS

This is a National Phase Application filed under 35 U.S.C. 371 as a national stage of PCT/CN2015/092686 filed Oct. 23, 2015, an application claiming the benefit under 35 USC 119(e) to the following U.S. Provisional Applications No. 62/068,298 filed Oct. 24, 2014, the content of each of which is hereby incorporated by reference in its entirety.

FIELD OF THE INVENTION

The present invention provides new clinical indication of several anti-biotic drugs, which were approved by FDA several years ago. The present invention demonstrates that several anti-biotic drugs can inhibit a variety of cancers effectively.

BACKGROUND OF THE INVENTION

Cancer is the most popular disease cause of death in the world. The cancer patients are gradually increase yearly, therefore the treatment method of the cancer has become an important issue. The medical treatments of cancer can be classified as surgical treatment, radiation therapy, chemotherapy and target therapy.

Generally, the cancer drug, whether chemotherapy drug or target therapy drug, is inhibit the cancer cells' duplication and split to prevent the tumor growth and metastasis. In clinical treatment options, the combination of chemotherapies and several targeted therapies were selected; try to eliminate cancer cells more effectively, by means of different mechanisms. Furthermore, if the cancer patients happen the drug resistance, that would reduce the effectiveness of the drugs and result in the medical treatment failure.

Antibiotic drugs, are a kind of secondary metabolite compounds produced by microorganisms (including bacteria, fungi, antinomycetes genus) and chemically synthesized compounds or semisynthetic similar compounds, used to inhibit the growth of other types of microbial. It is a broader concept for antibiotics in definition, which includes anti-bacterial antibiotics, antifungal and other antibiotics against tiny pathogens. However, in clinical practice, the antibiotics often refer to anti-bacterial antibiotics.

Based on the many years' experience of inventors, the human cancer cells and normal cells often have different characteristics, the differences in patterns or mechanism variation might be seen as a foreign invader. The different cancel cells are located in different locations and the statuses of variations are related to the located environment. Thus, the inventors are the first person to propose the use of antibiotic drugs to inhibit the cancer cell growth.

In contrast, these antibiotics have been used for decades and are recognized by FDA long time ago. These drugs already have been researched and analyzed to know the mechanism on human body. Therefore, the new invention would be time-saving and cost effective if these drugs applied in treating cancer. Besides, the treatment effect would be improved if these drugs are used to combine with other treating method.

After U.S. Provisional Application of the present invention was applied, there was another professor researched the possibility of this invention. There are lots of studies proposed and confirmed the effect of the present invention recently. According to the hypothesis proposed by the professor (which is similar to Endosymbiotic Theory), which proved that the mitochondria ever was one kind of bacteria and had been endocrine by larger bacteria, and then lived within the larger cell symbiotically. Thus, the mitochondria is different with the other cell organelle, mitochondria has its own gene, and is similar to prokaryotes (such as bacteria). This difference might be designed as a therapeutic drug to treat the cancer cell individually.

Recently, the drug design for cancer is mainly focused on development of high-specific drug molecules or target-based antibody. Averagely, only about five of 10,000 new drugs can successfully enter the phase I of clinical trials.

Otherwise, the manufacturing of the drug is also a big problem. When the drug starting the clinical trials, there are lots of problems need to overcome, such as drug safety, patient selection, trial dose and other issues. Even the drug has approved by the FDA and sales on the market, there still possibly face the situation of the poor drug response in patients. Furthermore, if the cancer patients happen the drug resistance, that would reduce the effectiveness of the drugs and result in the medical treatment failure. Therefore, the new drug development is very difficult.

SUMMARY OF THE INVENTION

To solve the above mentioned problem, the present invention provides a new usage of existing drugs through clinical trials of many kinds of drugs on new indications.

The experiment results showed that the antibiotic drugs had no toxicity or only little toxicity on normal cells. However, there are more studies need to be test to know that whether the antibiotic drugs have selection preference between normal cells and cancer cells. Besides, not all the antibiotic drugs could inhibit the growth of cancer cells under same condition, there are still lots of problems need to be overcame.

Term Definition

The antibiotic drugs are classified as nine categories by the structures, includes: aminoglycosides antibiotic drug, anti-fungal antibiotic drug, Cephalosporin antibiotic drug, β-propionamide antibiotic drug, chloramphenicol antibiotic drug, erythromycin antibiotic drug, penicillin antibiotic drug, tetracyclines antibiotic drug and other antibiotic drugs.

(1) Aminoglycosides antibiotic drug. Aminoglycoside is one class of antibiotics contains aminosugar substructures and cyclic amino alcohols, which is used to against Gram-negative bacteria and Pseudomonas aeruginosa clinically. The aminoglycosides antibiotic drugs which used in the present invention contains Amikacin sulfate, Amikacin hydrate, Netilmicin Sulfate.

(2) Anti-fungal antibiotic drug. Anti-fungal antibiotic drug is an antibiotics category against fungus. The anti-fungal antibiotic drugs of the present invention contains Posaconazole, Artemisinin, Fluconazole, Ketoconazole, Voriconazole, Natamycin (Pimaricin), Clotrimazole (Canesten), Amphotericin B (Abelcet),Flucytosine (Ancobon), Amorolfine Hydrochloride, Terbinafine (Lamisil, Terbinex), Butoconazole nitrate, Chloroxine, Bifonazole, Tioconazole, Nystatin (Mycostatin), Miconazole nitrate, Liranaftate,Isoconazole nitrate (Travogen), Terbinafine hydrochloride (Lamisil), Ciclopirox ethanolamine, Caspofungin acetate, Naftifine HCl, Sertaconazole nitrate, Pyrithione zinc, Sulconazole Nitrate, Climbazole, Valnemulin HCl;

(3) Cephalosporin antibiotic drug. Cephalosporins is part of a series of β-lactam antibiotics, and is classified as cephem together with cefotaxime. The Cephalosporin antibiotic drugs are used in the present invention contains: Cefdinir (Omnicef), Cefoperazone (Cefobid), Cefditoren pivoxil, Cephalexin (Cefalexin), Cefoselis sulfate, Ceftiofur hydrochloride, Cefaclor (Ceclor), Ceftazidime Pentahydrate, Moxalactam Disodium, Cephapirin Sodium (4) Beta-lactam antibiotic drug is a kind of very broad antibiotics, which features as penicillin and its derivatives, cephalosporins, monobactams, carbapenem and carbapenem enzyme inhibitors. Basically, all the β-lactam nucleus structure containing antibiotic drugs are classified as β-lactam antibiotics. It is the most widely used antibiotic drugs in conventional antibiotics. The Beta-lactam antibiotic drugs are used in the present invention contains Doripenem Hydrate, Meropenem, Aztreonam, Sulbactam, Sulbactam sodium (Unasyn), Biapenem;

(5) Chloramphenicol antibiotic drug. Chloramphenicol antibiotic drug has a very wide range of activity, which can be used to against gram-positive bacteria, including most of methicillin-resistant staphylococcus aureus, gram-negative bacteria and anaerobes. The Chloramphenicol antibiotic drugs are used in the present invention contains: Gatifloxacin, Daptomycin, Sulfapyridine (Dagenan), Sulfameter (Bayrena), Chloramphenicol (Chloromycetin).

(6) Penicillin antibiotic drug. Penicillin drug refers to a penicillanic containing molecule, which can destroy the cell walls of bacteria, can kill bacteria during the reproduction stage of bacteria, which is extracted from Penicillium. The Penicillin antibiotic drug belongs to β-lactam antibiotics. β-lactam antibiotic drugs include penicillins, cephalosporins, carbapenems, monocyclic and cephamycins. The Penicillin antibiotic drugs are used in the present invention contains Amoxicillin sodium (Amox), Ampicillin sodium, Carbenicillin disodium, Dicloxacillin Sodium, Ampicillin Trihydrate, Benzylpenicillin sodium, Mezlocillin Sodium, Piperacillin Sodium.

(7) Erythromycin antibiotic drug is a macrolide antibiotic drug. The antibacterial range of the erythromycin antibiotic drug is similar to penicillin. The erythromycin antibiotic drug has been mainly used for penicillin resistant staphylococcus, streptococcus, diarrhea and other gastrointestinal reaction induced bacteria. The Erythromycin antibiotic drugs are used in the present invention contains Teicoplanin, Linezolid (Zyvox), Erythromycin (E-Mycin), Erythromycin Ethylsuccinate, Spiramycin, Tilmicosin, Azithromycin Dihydrate, Dirithromycin, Fidaxomicin;

(8) Tetracyclines antibiotic drug. Tetracyclines antibiotic drug is a broad-spectrum antibiotic drugs family, which is named for the hydrogenated naphthacene nucleus. This class of drugs have broad spectrum and strong activity against Gram-negative bacteria, gram-positive bacteria, spirochetes, Chlamydia, Rickettsia, Mycoplasma, actinomycetes and amoeba. The Tetracyclines antibiotic drugs are used in the present invention contains Marbofloxacin, Moxifloxacin hydrochloride, Oxytetracycline (Terramycin), Tigecycline, Oxytetracycline dihydrate, Tetracycline HCl, Chlortetracycline HCl, Minocycline HCl, Rolitetracycline.

The present invention provides a usage of several antibiotic drugs for preparation of cancer inhibition pharmaceutical composition (drug), wherein the pharmaceutical composition is composed of an effective dosage of anti-biotic drug and a pharmaceutical acceptable salt.

The antibiotic drugs of the present invention are selected from aminoglycosides antibiotic drug, anti-fungal antibiotic drug, Cephalosporin antibiotic drug, β-propionamide antibiotic drug, chloramphenicol antibiotic drug, erythromycin antibiotic drug, penicillin antibiotic drug, tetracycline antibiotic drug and other antibiotic drugs.

In one embodiment of the present invention, the aminoglycosides antibiotic drug is selected from Amikacin sulfate, Amikacin hydrate, and Netilmicin Sulfate.

In one embodiment of the present invention, the anti-fungal antibiotic drug is selected from Posaconazole, Artemisinin, Fluconazole, Ketoconazole, Voriconazole, Natamycin (Pimaricin), Clotrimazole (Canesten), Amphotericin B (Abelcet), Flucytosine (Ancobon), Amorolfine Hydrochloride, Terbinafine (Lamisil, Terbinex), Butoconazole nitrate, Chloroxine, Bifonazole, Tioconazole, Nystatin (Mycostatin), Miconazole nitrate, Liranaftate, Isoconazole nitrate (Travogen), Terbinafine hydrochloride (Lamisil), Ciclopirox ethanolamine, Caspofungin acetate, Naftifine HCl, Sertaconazole nitrate, Pyrithione zinc, Sulconazole Nitrate, Climbazole, and Valnemulin HCl.

In one embodiment of the present invention, the Cephalosporin antibiotic drug is selected from Cefdinir (Omnicef), Cefoperazone (Cefobid), Cefditoren pivoxil, Cephalexin (Cefalexin), Cefoselis sulfate, Ceftiofur hydrochlorid, Cefaclor (Ceclor), Ceftazidime Pentahydrate, Moxalactam Disodiu, and Cephapirin Sodium.

In one embodiment of the present invention, the β-propionamide antibiotic drug is selected from Doripenem Hydrate, Meropenem, Aztreonam, Sulbactam, Sulbactam sodium (Unasyn), and Biapenem.

In one embodiment of the present invention, the chloramphenicol antibiotic drug is selected from Gatifloxacin, Daptomycin, Sulfapyridine (Dagenan), Sulfameter (Bayrena), and Chloramphenicol (Chloromycetin).

In one embodiment of the present invention, the penicillin antibiotic drug is selected from Amoxicillin sodium (Amox), Ampicillin sodium, Carbenicillin disodium, Dicloxacillin Sodium, Ampicillin Trihydrate, Benzylpenicillin sodium, Mezlocillin Sodium, Piperacillin Sodium.

In one embodiment of the present invention, the erythromycin antibiotic drug is selected from Teicoplanin, Linezolid (Zyvox), Erythromycin (E-Mycin), Erythromycin Ethylsuccinate, Spiramycin, Tilmicosin, Azithromycin Dihydrate, Dirithromycin, and Fidaxomicin.

In one embodiment of the present invention, the tetracyclines antibiotic drug is selected from Marbofloxacin, Moxifloxacin hydrochloride, Oxytetracycline (Terramycin), Tigecycline, Oxytetracycline dihydrate, Tetracycline HCl, Chlortetracycline HCl, Minocycline HCl, Rolitetracycline.

In one embodiment of the present invention, the other antibiotic drug is selected from Norfloxacin (Norxacin), Enoxacin (Penetrex), Pefloxacin mesylate, Sparfloxacin, Levofloxacin (Levaquin), Sarafloxacin HCl, Nalidixic acid (NegGram), Lomefloxacin hydrochloride (Maxaquin), Enrofloxacin, Clinafloxacin (PD127391), Orbifloxacin, Clinafoxacin HCl, Piromidic Acid, Cinoxacin, Difloxacin HCl, Rifabutin (Mycobutin), Rifapentine (Priftin), Pyrazinamide (Pyrazinoic acid amide), Rifampin (Rifadin, Rimactane), Ethionamide, Rifaximin (Xifaxan), Protionamide (Prothionamide), Isoniazid (Tubizid), D-Cycloserine, Streptomycin sulfate, Clofazimine, Nitrofurazone, Sulfanilamide, Sulfadiazine, Metronidazole (Flagyl), Sulfamethoxazole, Sulfisoxazole, Sulfamethizole (Proklar), Sulfadimethoxine, Clindamycin phosphate, Fenbendazole (Panacur), Sulfadoxine (Sulphadoxine), Secnidazole (Flagentyl), Clindamycin palmitate HCl, Clindamycin, Sulfathiazole, Trimethoprim, Sulfamerazine, Pentamidine, Colistin Sulfate (polypeptide), toltrazuril, tinidazoleMequinol, Bacitracin, Cetylpyridinium Chloride, Sulfaguanidine, Paromomycin Sulfate, Domiphen Bromide, Chlorquinaldol, Furaltadone HCl, Primaquine Diphosphate, Carbadox, Colistimethate Sodium, Meclocycline Sulfosalicylate, Thiostrepton, Bekanamycin, Clofoctol, Ritonavir, Entecavir hydrate, Artemisinin, Megestrol Acetate, Lansoprazole, Lopinavir (ABT-378), Ondansetron hydrochloride, Resveratrol, Stavudine, Tenofovir Disoproxil Fumarate, Tenofovir (Viread), Cidofovir (Vistide), Telaprevir (VX-950), Saxagliptin (BMS-477118,Onglyza), Darunavir Ethanolate (Prezista), Docosanol (Abreva), Amprenavir (Agenerase), Telbivudine (Sebivo, Tyzeka), Hydrocortisone (Cortisol), Didanosine (Videx), Emtricitabine (Emtriva), Lamivudine (Epivir), Adefovir Dipivoxil (Preveon, Hepsera), Zalcitabine, Prednisolone (Hydroretrocortine), Nevirapine (Viramune), Trifluridine (Viroptic), Vidarabine (Vira-A), Acyclovir (Aciclovir), Albendazole Oxide (Ricobendazole), Chenodeoxycholic acid, Valaciclovir HCl, Ganciclovir, Idoxuridine, Crystal violet, Rimantadine (Flumadine), Taurine (organic acid), Diclazuril (anticoccidial drug), Rebamipide, Orphenadrine citrate (Norflex), Terazosin HCl (Hytrin), Lafutidine, Dextrose, BIBR-1048 (Dabigatran), Rosuvastatin calcium (Crestor), Ammonium Glycyrrhizinate (AMGZ), Amfebutamone (Bupropion), Clonidine hydrochloride (Catapres), Fluocinolone acetonide (Flucort-N), Loperamide hydrochloride, Mycophenolic (Mycophenolate), Olanzapine (Zyprexa), Racecadotril (Acetorphan), Rosiglitazone maleate, Salbutamol sulfate (Albuterol), Tenoxicam (Mobiflex), Vardenafil (Vivanza), Dopamine hydrochloride (Inotropin), Ritodrine hydrochloride (Yutopar), Riboflavin (Vitamin B2), Clomipramine hydrochloride (Anafranil), Tiotropium Bromide hydrate, Isoprenaline hydrochloride, Medroxyprogesterone acetate, Xylometazoline HCl, Phenacetin, Trazodone hydrochloride (Desyrel), Brompheniramine, Acemetacin (Emflex), Dabrafenib (GSK2118436), Paroxetine HCl, Zanamivir (Relenza), Niflumic acid, Medetomidine HCl, Diclofenac Potassium, Ulipristal, Indacaterol Maleate, Biotin (Vitamin B7), Sodium salicylate, Methylthiouracil, Darifenacin HBr, Benztropine mesylate, Abacavir sulfate, Antipyrine, Amitriptyline HCl, Azatadine dimaleate, Triflusal, Pemirolast (BMY 26517) potassium, Homatropine Bromide, Carbimazole, Spironolactone, Ropivacaine HCl, Escitalopram oxalate, Bismuth Subcitrate Potassium(mineral), Chlorpropamide, Nifuroxazide, Penciclovir, Salicylanilide, Betamipron, Ethacridine lactate monohydrate (aromatic compound), Aminothiazole, Florfenicol, Cetrimonium Bromide (antiseptic), Thonzonium Bromide(detergent), and Pasiniazid.

In one embodiment of the present invention, the cancer is selected from lung cancer, gastrointestinal tract cancer, colorectal cancer, prostate cancer, bladder cancer, cervical cancer, breast cancer and blood cancer.

In one embodiment of the present invention, the effective dose of anti-biotic drug is from 20 mg/kg/day to 500 mg/kg/day.

The cancer drugs often cost hundreds of thousands to millions dollars nowadays. On the other hand, the cheaper antibiotic drugs are used for a long time. If the efficacy of anti-tumor treatment with using these antibiotic drugs is further confirmed, the new indication of the antibiotic drugs would bring hopes for the patients who cannot afford expensive drugs.

BRIEF DESCRIPTION OF THE DRAWINGS

FIG. 1 shows the results of the inhibitory effect of the cancer cells by antibiotic drugs.

DETAILED DESCRIPTION OF THE INVENTION

Cell Culture

Subculture the different types of cancer cells. The cancer cells includes lung cancer, gastric cancer, hepatic cancer, colon cancer, skin cancer, cervical cancer, prostate cancer, bladder cancer, breast cancer, leukemia, pancreatic cancer, ovarian cancer, tongue cancer, osteosarcoma, and renal cancer. The normal cells used in the control group included renal cell (HEK293), HFW human fibroblast cell line, human bronchial epithelial cell line BEAS-2B. (as shown in Table 1). Cancer cell lines were cultured in different culture medium according to different characteristics (as shown in Table 1). The cell numbers were counted and reseed as $2\times10^6$ in cell culture plate/flask. Then, the culture medium for culturing the cell lines was added to a volume of 10 ml, and the cells were cultured for 2-3 days. Then, the cells were suspended for loading into 96-well plates. The cell number was 3000 cells and the volume of the culture medium was 100 µl each well.

TABLE 1

Cancer cell lines and the culture medium

| No | Cancer type | Cancer cell type | medium |
|---|---|---|---|
| 1 | Lung cancer | HI650 (Lung Adenocarcinoma) | RPMI-1640 |
|   |   | A549 (Lung Adenocarcinoma) | DMEM |
| 2 | gastric cancer | AGS (Gastric Adenocarcinoma) | RPMI-1640 |
|   |   | MKN-45 (Gastric Adenocarcinoma) | RPMI-1640 |
| 3 | hepatic cancer | HepG2 (Hepatocellular Carcinoma) | DMEM |
|   |   | Hep3B (hepatocellular carcinoma) | DMEM |
| 4 | colon cancer | HCT116 (p53+) (Colorectal Carcinoma) | DMEM |
|   |   | LoVo (Colorectal Adenocarcinoma) | DMEM |
| 5 | skin cancer | A375 (Amelanotic Melanoma) | DMEM |
|   |   | BCC (basal cell carcinoma) | DMEM |
| 6 | cervical cancer | HeLa (Cervix Adenocarcinoma) | DMEM |
|   |   | C-33A (Cervical carcinoma) BCRC60554 | MEM |
| 7 | prostate cancer | PC3 (p53−) (Prostate Adenocarcinoma) | DMEM |
|   |   | LNCaP clone FGC (LNCap.FGC) | RPMI-1640 |
| 8 | bladder cancer | TSGH-8301 (Urinary Bladder Carcinoma) | RPMI-1640 |
|   |   | T24 | RPMI-1640 |
| 9 | breast cancer | MCF7 (Mammary Gland, Adenocarcinoma) | DMEM |
|   |   | MDA-MB-231 (Mammary Gland, Adenocarcinoma) | DMEM |

TABLE 1-continued

Cancer cell lines and the culture medium

| 10 | pancreatic cancer | BxPC-3 | RPMI-1640 |
|---|---|---|---|
|  |  | AsPC-1 | RPMI-1640 |
| 11 | ovarian Cancer | NIH: OVCAR-3 | RPMI-1640 |
|  |  | TOV-21G | RPMI-1640 |
| 12 | tongue cancer | SAS (Tongue squamous cell carcinoma) | DMEM |
| 13 | osteosarcoma | U-2OS | DMEM |
| 14 | renal Cancer | 786-O (Renal adenocarcinoma) BCRC 60243 | RPMI-1640 |
| 19 | leukemia | HL-60 (Acute Promyelocytic Leukemia) | RPMI |

| No | Control cell type | Cell line | medium |
|---|---|---|---|
| 20 | renal cell | HEK293 (Kidney) | DMEM |
| 21 | fibroblast cell | HFW | DMEM |
| 22 | lung epithelial cells | BEAS-2B (Lung Epithelial) | RPMI-1640 |

Cell Viability Analysis

Removing the original culture medium from 96-well plate. Then add 100 μl of commercially drug at a concentration of 10 μM per well. After 72 hours, add the diluted WST-1 reagent to the well with 100 μ/well, and the diluted WST-1 reagent was acquired from the dilution of 9:1 medium and WST-1 stock reagent. Finally, the total volume of each well are 200 μl/well. Culture the 96-well plate at 37° C. for 30 to 90 minutes. Detecting and calculating the survival rate of each cancer cell lines with an ELISA reader at OD450 nm. The lower viability of cancer cells represents better inhibition effect via the drugs. Otherwise, the higher viability of cancer cells represents worse inhibition effect via the drugs.

Growth Inhibitory Effects on Cancer Cell Lines by Various Antibiotic Drugs in the Present Invention The antibiotic drugs are classified 9 categories. So, the antibiotic drugs including aminoglycosides antibiotic drug, anti-fungal antibiotic drug, Cephalosporin antibiotic drug, β-propionamide antibiotic drug, chloramphenicol antibiotic drug, erythromycin antibiotic drug, penicillin antibiotic drug, tetracycline antibiotic drug and other antibiotic drugs were tested and analyze the inhibit effect on cancer cell lines growth by cell viability analysis.

The test results showed obviously that growth inhibitory effects on cancer cell lines by various antibiotic drugs (as shown in Table 2).

TABLE 2

The antibiotic drugs which do not have significant inhibitory effect to cancer cells

| Antibiotic drugs | Inhibitory effect on cancer cell line |
|---|---|
| Artemisinin | 0 |
| Cefoselis sulfate | 0 |
| Doripenem Hydrate | 0 |
| Marbofloxacin | 0 |
| Moxifloxacin hydrochloride | 0 |
| Norfloxacin (Norxacin) | 0 |
| Flucytosine (Ancobon) | 0 |
| Amorolfine Hydrochloride | 0 |
| Chloramphenicol (Chloromycetin) | 0 |
| Hydrocortisone (Cortisol) | 0 |
| Terbinafine (Lamisil, Terbinex) | 0 |
| Valaciclovir HCl | 0 |
| Ganciclovir | 0 |
| Sulfamethizole (Proklar) | 0 |
| Sulbactam | 0 |
| Sulphadimethoxine | 0 |
| Rimantadine (Flumadine) | 0 |
| Racecadotril (Acetorphan) | 0 |

TABLE 2-continued

The antibiotic drugs which do not have significant inhibitory effect to cancer cells

| Antibiotic drugs | Inhibitory effect on cancer cell line |
|---|---|
| Rosiglitazone maleate | 0 |
| Salbutamol sulfate (Albuterol) | 0 |
| Sulfadoxine (Sulphadoxine) | 0 |
| Tenoxicam (Mobiflex) | 0 |
| Ritodrine hydrochloride (Yutopar) | 0 |
| Brompheniramine | 0 |
| Acemetacin (Emflex) | 0 |
| Amikacin hydrate | 0 |
| Trimethoprim | 0 |
| Biotin (Vitamin B7) | 0 |
| Sulfamerazine | 0 |
| Sodium salicylate | 0 |
| Methylthiouracil | 0 |
| Benztropine mesylate | 0 |
| Triflusal | 0 |
| Carbimazole | 0 |
| Netilmicin Sulfate | 0 |
| Ropivacaine HCl | 0 |
| Erythromycin Ethylsuccinate | 0 |
| Escitalopram oxalate | 0 |
| Tinidazole | 0 |
| Bismuth Subcitrate Potassium | 0 |
| Sulfaguanidine | 0 |
| Mezlocillin Sodium | 0 |
| Penciclovir | 0 |
| Salicylanilide | 0 |
| Florfenicol | 0 |
| Dirithromycin | 0 |
| Piromidic Acid | 0 |

Besides, the inhibitory effect of all kinds antibiotic drugs on cancer cells are not the same (shown as FIG. 1). According to the experiment of the present invention, the Ritonavir, Entecavir hydrate, Posaconazole, Artemisinin, Megestrol Acetate, Fluconazole, Gatifloxacin, Ketoconazole, Lansoprazole, Acitretin, Biapenem, Cefoselis sulfate, Daptomycin, Doripenem Hydrate, Lopinavir (ABT-378), Meropenem, Ondansetron hydrochloride (Zofran), Resveratrol, Stavudine, Teicoplanin, Tenofovir Disoproxil Fumarate, Tenofovir (Viread), Tigecycline, Linezolid (Zyvox), Voriconazole, Marbofloxacin, Moxifloxacin hydrochloride, Cefaclor (Ceclor), Cephalexin (Cefalexin), Aztreonam (Azactam, Cayston), Norfloxacin (Norxacin), Cidofovir (Vistide), Natamycin (Pimaricin), Telaprevir (VX-950), Saxagliptin (BMS-477118,Onglyza), Cefdinir (Omnicef), Clotrimazole (Canesten), Cefoperazone (Cefobid), Sulfapyridine (Dagenan), Sulfameter (Bayrena), Darunavir Ethanolate (Prezista), Erythromycin (E-Mycin), Amphotericin B (Abelcet), Docosanol (Abreva), Amprenavir (Agenerase), Nitrofurazone (Nitrofural), Telbivudine (Sebivo, Tyzeka), Flucytosine (Ancobon), Amorolfine Hydrochloride, Chloramphenicol (Chloromycetin), Sulfanilamide, Hydrocortisone (Cortisol), Didanosine (Videx), Emtricitabine (Emtriva), Lamivudine (Epivir), Adefovir Dipivoxil (Preveon, Hepsera), Zalcitabine, Terbinafine (Lamisil, Terbinex), Prednisolone (Hydroretrocortine), Rifabutin (Mycobutin), Nevirapine (Viramune), Enoxacin (Penetrex), Rifapentine (Priftin), Pyrazinamide (Pyrazinoic acid amide), Rifampin (Rifadin, Rimactane), Cefditoren pivoxil, Sulfadiazine, Oxytetracycline (Terramycin), Ethionamide, Trifluridine (Vioptic), Vidarabine (Vira-A), Rifaximin (Xifaxan), Acyclovir (Aciclovir), Butoconazole nitrate, Albendazole Oxide (Ricobendazole), Chloroxine, Chenodeoxycholic acid, Bifonazole, Pefloxacin mesylate, Valaciclovir HCl, Ganciclovir, Protionamide (Prothionamide), Idoxuridine, Sparfloxacin, Metronidazole (Flagyl), Tioconazole, Sulfamethoxazole, Sulfisoxazole, Crystal violet, Nystatin (Mycostatin), Isoniazid (Tubizid), Levofloxacin (Levaquin), Miconazole nitrate, Sulfamethizole (Proklar), Sulbactam, Sulphadimethoxine, Rimantadine (Flumadine), Sarafloxacin HCl, Liranaftate, D-Cycloserine, Taurine, Diclazuril, Rebamipide, Clindamycin phosphate, Oxytetracycline dihydrate, Orphenadrine citrate (Norflex), Terazos in HCl (Hytrin), Lafutidine, Dextrose (D-glucose), BIBR-1048 (Dabigatran), Rosuvastatin calcium (Crestor), Nalidixic acid (NegGram), Ammonium Glycyrrhizinate (AMGZ), Amfebutamone (Bupropion), Clonidine hydrochloride (Catapres), Fenbendazole (Panacur), Fluocinolone acetonide (Flucort-N), Loperamide hydrochloride, Mycophenolic (Mycophenolate), Olanzapine (Zyprexa), Racecadotril (Acetorphan), Rosiglitazone maleate, Salbutamol sulfate (Albuterol), Sulfadoxine (Sulphadoxine), Tenoxicam (Mobiflex), Vardenafil (Vivanza), Dopamine hydrochloride (Inotropin), Ritodrine hydrochloride (Yutopar), Isoconazole nitrate (Travogen), Secnidazole (Flagentyl), Lomefloxacin hydrochloride (Maxaquin), Riboflavin (Vitamin B2), Clomipramine hydrochloride (Anafranil), Ceftiofur hydrochloride, Tiotropium Bromide hydrate, Sulbactam sodium (Unasyn), Terbinafine hydrochloride (Lamisil), Amoxicillin sodium (Amox), Isoprenaline hydrochloride, Medroxyprogesterone acetate, Streptomycin sulfate, Tetracycline HCl, Xylometazoline HCl, Phenacetin, Trazodone hydrochloride (Desyrel), Brompheniramine, Clindamycin palmitate HCl, Acemetacin (Emflex), Dabrafenib (GSK2118436), Clindamycin, Paroxetine HCl, Zanamivir (Relenza), Niflumic acid, Ciclopirox ethanolamine, Enrofloxacin, Medetomidine HCl, Diclofenac Potassium, Amikacin sulfate, Caspofungin acetate, Ulipristal, Indacaterol Maleate, Sulfathiazole, Amikacin hydrate, Trimethoprim, Biotin (Vitamin B7), Sulfamerazine, Sodium salicylate, Methylthiouracil, Darifenacin HBr, Naftifine HCl, Sertaconazole nitrate, Benztropine mesylate, Abacavir sulfate, Ampicillin sodium, Antipyrine, Carbenicillin disodium, Amitriptyline HCl, Azatadine dimaleate, Triflusal, Clinafloxacin (PD127391), Pentamidine, Pemirolast (BMY 26517) potassium, Homatropine Bromide, Colistin Sulfate, toltrazuril, Carbimazole, Netilmicin Sulfate, Spironolactone, Ropivacaine HCl, Erythromycin Ethylsuccinate, Escitalopram oxalate, tinidazole, Pyrithione zinc, Mequinol, Spiramycin, Bismuth Subcitrate Potassium, Clofazimine, Dicloxacillin Sodium, Sulconazole Nitrate, Tilmicosin, Bacitracin, Azithromycin Dihydrate, Ampicillin Trihydrate, Orbifloxacin, Chlortetracycline HCl, Benzylpenicillin sodium, Chlorpropamide, Cetylpyridinium Chloride, Sulfaguanidine, Climbazole, Mezlocillin Sodium, Nifuroxazide, Paromomycin Sulfate, Penciclovir, Domiphen Bromide, Salicylanilide, Betamipron, Chlorquinaldol, Ethacridine lactate monohydrate, Aminothiazole, Florfenicol, Furaltadone HCl, Dirithromycin, Valnemulin HCl, Piperacillin Sodium, Minocycline HCl, Fidaxomicin, Primaquine Diphosphate, Cetrimonium Bromide, Carbadox, Ceftazidime Pentahydrate, Clinafoxacin HCl, Colistimethate Sodium, Meclocycline Sulfosalicylate, Moxalactam Disodium, Piromidic Acid, Rolitetracycline, Thiostrepton, Thonzonium Bromide, Cinoxacin, Bekanamycin, Difloxacin HCl, Cephapirin Sodium, Clofoctol, Pasiniazid showed significant inhibition effect on different cancer cell lines (shown as Table 3).

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 3

The results of antibiotic drug for inhibiting cancer cell lines

| Drug Name | A375 | HCT116 | HepG2 | HeLa | AGS | H1650 | MKN-45 | TSGH | A549 | MCF7 | PC3 | LoVo | HL-60 |
|---|---|---|---|---|---|---|---|---|---|---|---|---|---|
| Ritonavir | 69.9 | 58.8 | 65.4 | 48.6 | 69.9 | 40.8 | 49.7 | 71.4 | 86.8 | 100.8 | 61.5 | 82.3 | 106.7 |
| Entecavir hydrate | 98.6 | 87.1 | 98.8 | 99.4 | 46.4 | 80.8 | 59.7 | 53.0 | 57.4 | 58.6 | 81.2 | 91.6 | 74.1 |
| Posaconazole | 49.8 | 65.4 | 87.2 | 75.8 | 42.7 | 67.0 | 52.0 | 51.3 | 42.9 | 63.6 | 45.3 | 73.7 | 71.3 |
| Artemisinin | 88.9 | 95.5 | 116.5 | 120.1 | 87.7 | 106.4 | 117.1 | 63.6 | 98.7 | 150.6 | 92.5 | 103.5 | 146.0 |
| Megestrol Acetate | 80.8 | 59.5 | 88.9 | 78.6 | 84.7 | 56.0 | 74.8 | 74.3 | 1116.1 | 109.9 | 80.3 | 108.9 | 94.0 |
| Fluconazole | 76.9 | 42.9 | 97.4 | 79.2 | 50.2 | 45.3 | 76.2 | 66.1 | 125.2 | 101.1 | 97.7 | 102.1 | 105.7 |
| Gatifloxacin | 63.3 | 57.4 | 65.6 | 84.1 | 71.4 | 47.2 | 84.2 | 65.0 | 96.0 | 130.2 | 82.2 | 98.3 | 100.5 |
| Ketoconazole | 49.2 | 38.1 | 88.7 | 84.3 | 65.7 | 46.1 | 77.0 | 107.3 | 75.7 | 118.0 | 80.1 | 90.3 | 88.3 |
| Lansoprazole | 60.6 | 57.9 | 72.3 | 53.6 | 71.5 | 45.5 | 74.5 | 109.0 | 84.5 | 141.3 | 94.2 | 96.1 | 78.6 |
| Acitretin | 61.4 | 47.9 | 72.6 | 52.7 | 68.1 | 43.8 | 78.5 | 126.6 | 69.1 | 118.6 | 92.5 | 83.6 | 96.7 |
| Biapenem | 60.4 | 78.3 | 66.4 | 54.0 | 75.1 | 42.2 | 81.5 | 117.3 | 90.1 | 135.6 | 80.3 | 88.7 | 95.5 |
| Cefoselis sulfate | 106.2 | 96.2 | 111.9 | 103.7 | 78.2 | 88.4 | 100.9 | 77.7 | 99.7 | 83.5 | 97.8 | 91.9 | 95.2 |
| Daptomycin | 81.2 | 90.8 | 95.9 | 113.6 | 63.0 | 76.3 | 92.1 | 56.8 | 74.0 | 85.3 | 79.7 | 90.9 | 108.3 |
| Doripenem Hydrate | 100.8 | 95.6 | 106.5 | 121.9 | 66.5 | 78.5 | 110.6 | 79.9 | 70.9 | 99.8 | 84.2 | 95.2 | 91.2 |
| Lopinavir (ABT-378) | 83.1 | 81.8 | 93.1 | 115.5 | 55.4 | 53.1 | 74.2 | 82.2 | 63.8 | 77.9 | 68.0 | 85.1 | 92.4 |
| Meropenem | 65.1 | 97.1 | 99.3 | 110.9 | 68.3 | 55.4 | 84.9 | 132.5 | 46.0 | 68.1 | 70.7 | 87.3 | 102.5 |
| Ondansetron HCl (Zofran) | 57.7 | 73.6 | 98.3 | 86.2 | 59.7 | 60.9 | 70.8 | 88.7 | 47.1 | 64.5 | 66.0 | 82.4 | 97.3 |
| Resveratrol | 53.0 | 74.3 | 101.1 | 108.2 | 47.9 | 54.6 | 91.8 | 85.3 | 72.5 | 71.8 | 75.0 | 83.2 | 76.4 |
| Stavudine | 56.1 | 73.1 | 97.1 | 98.1 | 39.2 | 50.2 | 66.8 | 111.5 | 38.9 | 56.6 | 73.5 | 70.7 | 96.0 |
| Teicoplanin | 64.1 | 64.4 | 94.7 | 86.5 | 58.7 | 47.6 | 70.0 | 81.7 | 51.7 | 64.2 | 83.5 | 82.1 | 96.8 |
| Tenofovir Disoproxil Fumarate | 67.1 | 68.4 | 93.7 | 85.7 | 54.7 | 50.9 | 71.6 | 88.2 | 47.0 | 68.7 | 66.9 | 75.8 | 93.4 |
| Tenofovir (Viread) | 60.6 | 81.8 | 99.0 | 95.0 | 67.0 | 55.6 | 70.9 | 92.4 | 47.7 | 71.1 | 68.1 | 85.9 | 97.6 |
| Tigecycline | 52.2 | 80.0 | 101.6 | 100.7 | 49.4 | 53.1 | 89.2 | 98.5 | 55.9 | 71.1 | 83.0 | 82.4 | 97.6 |
| Linezolid (Zyvox) | 57.6 | 76.7 | 91.3 | 93.7 | 70.8 | 51.3 | 65.9 | 58.2 | 40.2 | 66.3 | 67.0 | 91.0 | 129.4 |
| Voriconazole | 102.3 | 113.3 | 101.1 | 92.6 | 86.1 | 102.1 | 104.1 | 53.9 | 82.9 | 90.1 | 97.0 | 101.3 | 94.3 |
| Marbofloxacin | 86.8 | 95.1 | 95.6 | 88.2 | 81.2 | 80.3 | 112.0 | 91.6 | 83.8 | 92.3 | 78.4 | 107.9 | 104.8 |
| Moxifloxacin hydrochloride | 94.0 | 90.1 | 95.2 | 92.0 | 77.1 | 70.9 | 89.0 | 75.7 | 95.5 | 90.3 | 69.1 | 102.2 | 97.1 |
| Cefaclor (Ceclor) | 67.5 | 93.4 | 108.1 | 86.7 | 41.9 | 62.3 | 97.0 | 81.6 | 61.0 | 90.6 | 70.1 | 88.2 | 112.1 |
| Cephalexin (Cefalexin) | 92.7 | 107.2 | 109.0 | 76.2 | 59.6 | 71.2 | 94.9 | 69.2 | 80.6 | 96.1 | 57.5 | 85.9 | 95.2 |
| Aztreonam (Azactam, Cayston) | 88.6 | 80.4 | 110.8 | 87.2 | 40.9 | 48.6 | 60.5 | 52.3 | 56.9 | 68.6 | 55.2 | 76.3 | 113.0 |
| Norfloxacin (Norxacin) | 73.8 | 99.0 | 90.5 | 78.7 | 63.8 | 75.0 | 68.9 | 75.9 | 84.8 | 94.8 | 72.2 | 88.0 | 87.7 |
| Cidofovir (Vistide) | 82.6 | 88.0 | 97.2 | 82.1 | 39.6 | 53.3 | 56.9 | 49.8 | 58.3 | 78.3 | 63.9 | 82.3 | 112.2 |
| Natamycin (Pimaricin) | 82.1 | 89.3 | 95.3 | 93.5 | 40.9 | 57.0 | 67.1 | 84.9 | 62.6 | 83.2 | 70.0 | 84.8 | 106.9 |
| Telaprevir (VX-950) | 130.7 | 81.0 | 100.4 | 84.0 | 49.2 | 51.6 | 48.0 | 50.2 | 49.3 | 61.6 | 50.0 | 73.7 | 111.4 |
| Saxagliptin (BMS-477118, Onglyza) | 90.8 | 81.2 | 94.9 | 81.2 | 40.9 | 49.5 | 49.4 | 56.9 | 43.1 | 55.2 | 65.8 | 80.0 | 108.5 |
| Cefdinir (Omnicef) | 92.5 | 94.2 | 105.5 | 86.4 | 79.1 | 93.6 | 70.5 | 35.6 | 97.0 | 55.1 | 134.7 | 110.7 | 104.1 |
| Clotrimazole (Canesten) | 81.4 | 67.0 | 101.8 | 90.0 | 85.7 | 75.9 | 53.9 | 50.8 | 85.5 | 56.8 | 69.3 | 94.1 | 106.4 |
| Cefoperazone (Cefobid) | 90.0 | 85.3 | 100.8 | 91.7 | 98.6 | 98.4 | 51.6 | 60.3 | 76.5 | 50.1 | 104.3 | 105.3 | 111.1 |
| Sulfapyridine (Dagenan) | 77.2 | 82.2 | 98.9 | 71.2 | 71.9 | 69.5 | 53.8 | 64.6 | 64.5 | 54.7 | 107.8 | 84.6 | 111.1 |
| Sulfameter (Bayrena) | 89.2 | 81.5 | 95.5 | 78.4 | 67.4 | 84.8 | 58.6 | 78.6 | 59.0 | 51.7 | 90.2 | 89.9 | 109.5 |
| Darunavir Ethanolate (Prezista) | 79.9 | 70.0 | 90.5 | 79.2 | 75.4 | 82.2 | 62.6 | 46.7 | 72.6 | 43.9 | 87.8 | 98.8 | 114.9 |
| Erythromycin (E-Mycin) | 100.8 | 77.7 | 93.5 | 93.0 | 27.7 | 90.4 | 53.2 | 42.6 | 63.8 | 45.2 | 86.0 | 85.5 | 110.7 |

TABLE 3-continued

The results of antibiotic drug for inhibiting cancer cell lines

| Drug | 1 | 2 | 3 | 4 | 5 | 6 | 7 | 8 | 9 | 10 | 11 | 12 | 13 |
|---|---|---|---|---|---|---|---|---|---|---|---|---|---|
| Amphotericin B (Abelcet) | 98.9 | 57.4 | 90.3 | 84.5 | 28.5 | 61.2 | 44.0 | 56.0 | 45.0 | 38.9 | 66.9 | 66.5 | 115.6 |
| Docosanol (Abreva) | 84.6 | 65.7 | 83.6 | 76.9 | 40.6 | 69.3 | 52.4 | 54.8 | 44.0 | 39.1 | 70.2 | 89.4 | 115.7 |
| Amprenavir (Agenerase) | 77.6 | 68.0 | 90.9 | 67.5 | 58.8 | 69.5 | 52.1 | 57.0 | 53.7 | 37.0 | 80.4 | 77.4 | 111.0 |
| Nitrofurazone (Nitrofural) | 54.9 | 65.0 | 82.4 | 55.4 | 28.0 | 61.1 | 42.0 | 32.5 | 44.3 | 35.3 | 53.8 | 64.9 | 85.6 |
| Telbivudine (Sebivo, Tyzeka) | 57.5 | 51.2 | 94.4 | 51.9 | 27.5 | 67.5 | 36.2 | 50.4 | 43.7 | 31.9 | 53.6 | 65.3 | 100.5 |
| Flucytosine (Ancobon) | 101.5 | 84.0 | 93.2 | 80.9 | 70.7 | 92.1 | 72.9 | 93.9 | 91.4 | 75.3 | 107.6 | 107.5 | 102.2 |
| Amorolfine Hydrochloride | 98.6 | 86.5 | 91.6 | 84.6 | 94.4 | 79.6 | 65.1 | 88.5 | 104.5 | 104.3 | 103.7 | 99.7 | 103.5 |
| Chloramphenicol (Chloromycetin) | 114.0 | 92.7 | 93.6 | 85.0 | 90.6 | 75.6 | 66.8 | 83.5 | 96.3 | 89.1 | 119.5 | 100.8 | 105.4 |
| Sulfanilamide | 84.6 | 98.9 | 100.7 | 82.1 | 65.3 | 66.7 | 59.1 | 76.5 | 82.7 | 104.9 | 111.0 | 85.0 | 112.2 |
| Hydrocortisone (Cortisol) | 87.6 | 97.4 | 108.8 | 86.1 | 77.5 | 66.1 | 81.3 | 125.3 | 73.6 | 76.9 | 103.8 | 83.3 | 104.8 |
| Didanosine (Videx) | 77.2 | 130.4 | 119.1 | 80.3 | 48.7 | 64.2 | 62.0 | 76.7 | 67.5 | 78.4 | 76.4 | 95.1 | 126.5 |
| Emtricitabine (Emtriva) | 84.0 | 113.3 | 110.1 | 79.6 | 48.0 | 61.0 | 62.8 | 85.3 | 86.9 | 74.0 | 77.1 | 82.6 | 119.4 |
| Lamivudine (Epivir) | 95.8 | 102.2 | 107.7 | 86.4 | 44.7 | 54.1 | 47.7 | 71.1 | 75.2 | 83.2 | 110.5 | 71.3 | 119.0 |
| Adefovir Dipivoxil (Preveon, Hepsera) | 81.7 | 94.5 | 95.5 | 96.6 | 35.1 | 55.3 | 46.1 | 47.0 | 47.3 | 56.7 | 91.3 | 62.0 | 60.4 |
| Zalcitabine | 83.5 | 147.3 | 96.9 | 89.2 | 69.1 | 86.4 | 70.4 | 79.0 | 66.3 | 52.7 | 101.0 | 91.0 | 118.7 |
| Terbinafine (Lamisil, Terbinex) | 99.7 | 103.8 | 98.3 | 65.2 | 136.7 | 103.5 | 142.8 | 109.1 | 115.2 | 103.9 | 140.5 | 94.0 | 95.2 |
| Prednisolone (Hydrocortocortine) | 71.0 | 76.6 | 82.7 | 78.7 | 124.0 | 82.5 | 67.8 | 86.2 | 71.3 | 45.5 | 83.3 | 92.5 | 99.0 |
| Rifabutin (Mycobutin) | 84.0 | 98.8 | 147.6 | 52.8 | 115.2 | 88.2 | 62.4 | 82.5 | 53.1 | 48.8 | 72.6 | 104.4 | 100.2 |
| Nevirapine (Viramune) | 66.8 | 76.6 | 85.5 | 58.9 | 114.9 | 89.7 | 68.3 | 102.7 | 45.7 | 38.5 | 84.1 | 85.7 | 98.7 |
| Enoxacin (Penetrex) | 66.9 | 78.9 | 88.1 | 68.5 | 110.7 | 92.3 | 54.3 | 90.4 | 45.8 | 44.5 | 111.6 | 83.8 | 108.1 |
| Rifapentine (Priftin) | 77.7 | 78.3 | 101.6 | 56.5 | 63.7 | 101.0 | 58.6 | 99.2 | 47.4 | 46.2 | 99.1 | 92.3 | 99.1 |
| Pyrazinamide | 58.6 | 55.4 | 88.1 | 54.3 | 74.9 | 79.1 | 53.6 | 88.3 | 33.9 | 40.9 | 100.5 | 56.9 | 106.4 |
| Rifampin (Rifadin, Rimactane) | 61.6 | 72.6 | 98.5 | 58.8 | 111.0 | 89.1 | 61.1 | 107.8 | 45.2 | 39.7 | 69.9 | 83.9 | 105.1 |
| Cefditoren pivoxil | 69.1 | 75.8 | 96.9 | 58.7 | 86.5 | 80.7 | 70.5 | 94.8 | 45.7 | 38.4 | 83.9 | 83.5 | 110.5 |
| Sulfadiazine | 79.5 | 52.5 | 113.6 | 43.7 | 91.8 | 69.2 | 44.4 | 80.4 | 38.1 | 37.2 | 70.1 | 93.6 | 106.1 |
| Oxytetracycline (Terramycin) | 51.2 | 77.9 | 88.4 | 51.2 | 61.9 | 70.1 | 56.7 | 73.8 | 42.3 | 38.9 | 70.8 | 86.6 | 97.9 |
| Ethionamide | 76.6 | 73.5 | 97.7 | 44.8 | 53.7 | 78.3 | 45.4 | 53.2 | 42.4 | 36.4 | 85.3 | 86.5 | 101.5 |
| Trifluridine (Viroptic) | 48.6 | 53.8 | 90.2 | 51.8 | 64.4 | 71.0 | 43.6 | 51.3 | 36.5 | 36.3 | 61.4 | 72.1 | 88.9 |
| Vidarabine (Vira-A) | 48.1 | 75.1 | 74.2 | 47.7 | 103.7 | 78.8 | 44.4 | 68.6 | 32.5 | 36.5 | 70.6 | 72.9 | 99.0 |
| Rifaximin (Xifaxan) | 59.5 | 63.7 | 101.9 | 54.0 | 93.2 | 82.4 | 52.7 | 61.3 | 35.1 | 40.1 | 67.1 | 89.1 | 100.3 |
| Acyclovir (Aciclovir) | 112.3 | 96.0 | 103.5 | 87.2 | 77.1 | 101.2 | 55.9 | 107.1 | 126.2 | 75.8 | 101.5 | 66.3 | 91.6 |
| Butoconazole nitrate | 101.9 | 116.3 | 114.0 | 131.3 | 105.8 | 78.2 | 48.7 | 86.0 | 89.6 | 72.9 | 57.1 | 112.3 | 41.3 |
| Albendazole Oxide (Ricobendazole) | 92.9 | 76.8 | 103.7 | 56.0 | 34.0 | 59.5 | 60.8 | 77.7 | 154.8 | 62.3 | 60.5 | 68.9 | 102.6 |
| Chloroxine | 72.5 | 65.4 | 93.9 | 71.7 | 31.1 | 77.1 | 52.7 | 62.7 | 119.5 | 68.7 | 87.2 | 85.5 | 50.5 |
| Chenodeoxycholic acid | 64.2 | 104.2 | 94.8 | 69.1 | 68.9 | 68.1 | 51.8 | 88.8 | 96.3 | 74.5 | 71.4 | 82.7 | 118.2 |
| Bifonazole | 94.9 | 111.8 | 109.4 | 67.2 | 64.3 | 55.9 | 50.5 | 82.1 | 79.3 | 73.3 | 78.2 | 81.1 | 119.4 |
| Pefloxacin mesylate | 98.2 | 114.1 | 107.6 | 61.3 | 77.1 | 54.7 | 51.6 | 89.4 | 76.1 | 62.9 | 73.2 | 80.3 | 126.4 |
| Valaciclovir HCl | 95.6 | 112.2 | 110.4 | 109.2 | 109.7 | 90.6 | 91.6 | 83.9 | 126.3 | 67.8 | 68.3 | 97.0 | 103.4 |
| Ganciclovir | 94.8 | 98.8 | 108.8 | 107.1 | 105.8 | 97.3 | 87.0 | 103.2 | 104.2 | 68.6 | 71.8 | 99.9 | 98.7 |
| Protionamide (Prothionamide) | 84.9 | 105.2 | 117.7 | 97.5 | 85.9 | 85.0 | 77.6 | 102.6 | 66.2 | 51.2 | 45.2 | 85.6 | 97.6 |
| Idoxuridine | 81.5 | 69.3 | 122.2 | 101.3 | 68.7 | 82.8 | 80.8 | 88.0 | 58.5 | 47.3 | 57.8 | 72.7 | 96.1 |
| Sparfloxacin | 82.6 | 85.4 | 97.6 | 88.3 | 79.9 | 88.5 | 57.5 | 68.1 | 86.5 | 56.3 | 50.1 | 97.0 | 99.3 |

TABLE 3-continued

The results of antibiotic drug for inhibiting cancer cell lines

| | | | | | | | | | |
|---|---|---|---|---|---|---|---|---|---|
| Metronidazole (Flagyl) | 56.4 | 104.6 | 90.7 | 90.5 | 94.9 | 57.7 | 62.0 | 36.5 | 43.8 | 40.9 | 61.1 | 90.8 |
| Tioconazole | 60.9 | 100.4 | 58.5 | 82.7 | 72.9 | 61.0 | 68.1 | 47.6 | 48.0 | 40.7 | 83.2 | 57.1 |
| Sulfamethoxazole | 44.3 | 115.4 | 87.8 | 67.7 | 85.8 | 60.7 | 62.1 | 43.9 | 46.1 | 44.9 | 71.7 | 99.4 |
| Sulfisoxazole | 65.5 | 87.8 | 78.9 | 88.7 | 73.9 | 48.4 | 93.0 | 39.4 | 46.1 | 36.1 | 68.8 | 95.2 |
| Crystal violet | 32.0 | 41.9 | 38.9 | 52.7 | 68.5 | 44.8 | 44.1 | 37.5 | 46.0 | 31.8 | 62.3 | 37.3 |
| Nystatin (Mycostatin) | 62.4 | 79.7 | 59.2 | 50.8 | 65.4 | 44.7 | 42.1 | 37.1 | 46.4 | 33.8 | 70.9 | 96.2 |
| Isoniazid (Tubizid) | 54.9 | 60.1 | 77.9 | 50.5 | 64.7 | 44.6 | 42.2 | 45.7 | 44.7 | 39.6 | 71.0 | 101.5 |
| Levofloxacin (Levaquin) | 39.3 | 40.3 | 50.8 | 51.6 | 64.9 | 44.5 | 41.8 | 36.7 | 43.9 | 29.6 | 62.6 | 93.0 |
| Miconazole nitrate | 31.5 | 105.4 | 57.6 | 51.1 | 68.8 | 45.0 | 41.8 | 37.3 | 50.7 | 30.4 | 62.1 | 41.4 |
| Sulfamethizole (Proklar) | 99.1 | 87.8 | 105.3 | 86.6 | 99.2 | 84.6 | 114.5 | 90.4 | 100.0 | 86.0 | 86.4 | 103.6 |
| Sulbactam | 84.5 | 75.9 | 102.8 | 80.5 | 67.0 | 77.8 | 133.1 | 81.1 | 108.5 | 105.9 | 81.7 | 104.1 |
| Sulphadimethoxine | 76.0 | 98.5 | 68.8 | 99.3 | 83.1 | 72.0 | 131.7 | 100.5 | 94.3 | 94.0 | 70.8 | 120.4 |
| Rimantadine (Flumadine) | 70.3 | 98.6 | 71.1 | 90.8 | 96.9 | 82.3 | 126.4 | 110.6 | 97.1 | 91.3 | 95.7 | 107.0 |
| Sarafloxacin HCl | 97.8 | 80.0 | 81.0 | 88.0 | 58.9 | 75.3 | 121.9 | 98.6 | 107.4 | 80.9 | 106.5 | 111.7 |
| Liranaftate | 84.5 | 50.4 | 89.0 | 73.6 | 50.7 | 76.7 | 108.3 | 67.1 | 84.8 | 92.7 | 86.6 | 92.0 |
| D-Cycloserine | 91.2 | 62.5 | 81.7 | 68.6 | 50.8 | 68.6 | 114.1 | 96.6 | 112.8 | 83.9 | 102.8 | 113.9 |
| Taurine | 77.6 | 56.1 | 84.9 | 64.1 | 46.1 | 61.6 | 109.8 | 84.0 | 91.5 | 61.1 | 98.5 | 115.7 |
| Diclazuril | 84.5 | 108.9 | 76.1 | 76.3 | 104.5 | 97.6 | 103.1 | 42.7 | 40.4 | 95.5 | 78.4 | 70.2 |
| Rebamipide | 81.1 | 88.1 | 77.4 | 89.6 | 80.4 | 97.4 | 105.4 | 28.0 | 39.1 | 82.2 | 84.9 | 100.0 |
| Clindamycin phosphate | 81.3 | 108.1 | 61.4 | 91.6 | 87.0 | 85.6 | 79.6 | 31.0 | 38.3 | 40.0 | 44.4 | 109.8 |
| Oxytetracycline dihydrate | 72.5 | 110.0 | 65.6 | 71.7 | 73.8 | 81.4 | 53.4 | 22.1 | 34.2 | 42.1 | 47.0 | 99.3 |
| Orphenadrine citrate | 89.2 | 117.1 | 67.9 | 82.9 | 99.6 | 101.7 | 53.4 | 21.8 | 35.9 | 41.6 | 45.6 | 92.9 |
| Terazosin HCl (Hytrin) | 77.9 | 97.2 | 60.7 | 56.8 | 74.9 | 82.1 | 71.6 | 21.3 | 33.4 | 40.5 | 45.7 | 110.8 |
| Lafutidine | 116.3 | 74.3 | 46.9 | 45.5 | 80.1 | 89.6 | 51.9 | 21.3 | 33.6 | 40.7 | 48.0 | 95.3 |
| Dextrose (D-glucose) | 77.0 | 121.4 | 74.4 | 58.4 | 71.1 | 83.9 | 78.8 | 80.9 | 93.2 | 95.0 | 85.3 | 104.3 |
| BIBR-1048 (Dabigatran) | 50.9 | 78.9 | 71.9 | 62.4 | 62.7 | 58.0 | 83.8 | 73.8 | 85.8 | 86.9 | 90.9 | 87.9 |
| Rosuvastatin calcium (Crestor) | 55.6 | 139.9 | 74.6 | 55.9 | 80.8 | 83.8 | 56.0 | 97.0 | 88.9 | 94.3 | 101.0 | 81.7 |
| Nalidixic acid (NegGram) | 87.9 | 78.9 | 95.8 | 57.3 | 72.0 | 54.9 | 46.3 | 83.8 | 86.0 | 74.6 | 91.5 | 113.3 |
| Ammonium Glycyrrhizinate (AMGZ) | 75.5 | 74.3 | 74.1 | 50.5 | 75.8 | 49.2 | 53.7 | 58.0 | 81.0 | 64.0 | 81.3 | 127.9 |
| Amfebutamone (Bupropion) | 88.2 | 79.1 | 53.4 | 30.0 | 74.3 | 52.1 | 44.9 | 59.2 | 64.7 | 62.8 | 51.4 | 117.9 |
| Clonidine hydrochloride (Catapres) | 62.5 | 25.6 | 72.0 | 36.4 | 64.1 | 48.8 | 28.5 | 37.3 | 68.8 | 40.7 | 72.1 | 127.5 |
| Fenbendazole (Panacur) | 40.6 | 34.1 | 38.6 | 29.9 | 60.2 | 40.3 | 27.2 | 40.9 | 55.8 | 42.0 | 52.9 | 66.6 |
| Fluocinolone acetonide (Flucort-N) | 45.8 | 26.3 | 46.0 | 30.0 | 58.4 | 34.9 | 38.3 | 52.5 | 54.2 | 40.7 | 52.3 | 116.3 |
| Loperamide hydrochloride | 58.8 | 65.5 | 73.0 | 57.3 | 66.7 | 64.3 | 42.7 | 104.2 | 78.9 | 64.7 | 64.8 | 100.8 |
| Mycophenolic Mycophenolate) | 57.4 | 47.8 | 90.7 | 57.8 | 83.1 | 61.7 | 40.3 | 80.6 | 120.5 | 74.3 | 70.1 | 65.6 |
| Olanzapine (Zyprexa) | 91.9 | 108.8 | 84.2 | 84.0 | 109.0 | 80.1 | 58.7 | 88.0 | 124.9 | 92.2 | 88.5 | 118.2 |
| Racecadotril (Acetorphan) | 66.2 | 109.8 | 84.0 | 84.0 | 82.9 | 97.4 | 65.6 | 95.8 | 107.9 | 106.7 | 74.5 | 121.5 |
| Rosiglitazone maleate | 70.3 | 96.1 | 83.3 | 113.1 | 87.7 | 73.7 | 85.2 | 79.1 | 114.3 | 121.3 | 93.5 | 109.2 |
| Salbutamol sulfate (Albuterol) | 98.0 | 100.8 | 99.9 | 91.8 | 84.3 | 71.2 | 62.3 | 94.6 | 139.6 | 107.9 | 97.1 | 104.1 |
| Sulfadoxine (Sulphadoxine) | 65.5 | 90.5 | 78.2 | 91.1 | 62.2 | 87.4 | 64.3 | 96.6 | 131.7 | 119.1 | 92.9 | 110.7 |
| Tenoxicam (Mobiflex) | 80.2 | 89.1 | 89.7 | 97.7 | 69.9 | 94.9 | 67.3 | 98.6 | 126.4 | 120.4 | 94.6 | 113.9 |
| Vardenafil (Vivanza) | 73.2 | 81.8 | 61.7 | 86.5 | 67.2 | 68.2 | 57.8 | 96.5 | 117.0 | 110.8 | 105.9 | 126.9 |
| Dopamine hydrochloride (Inotropin) | 83.0 | 100.8 | 85.1 | 74.3 | 76.0 | 85.0 | 57.7 | 101.8 | 148.3 | 115.2 | 84.3 | 91.5 |

TABLE 3-continued

The results of antibiotic drug for inhibiting cancer cell lines

| Drug | | | | | | | | | | | | | |
|---|---|---|---|---|---|---|---|---|---|---|---|---|---|
| Ritodrine hydrochloride (Yutopar) | 87.4 | 114.4 | 92.8 | 132.9 | 80.1 | 96.4 | 97.2 | 64.4 | 95.5 | 86.5 | 113.4 | 103.6 | 86.0 |
| Isoconazole nitrate (Travogen) | 95.0 | 129.5 | 99.4 | 165.3 | 74.8 | 102.2 | 125.7 | 88.2 | 91.7 | 95.1 | 82.5 | 101.7 | 49.2 |
| Secnidazole (Flagentyl) | 117.0 | 96.6 | 99.0 | 124.3 | 78.0 | 46.8 | 77.2 | 52.1 | 69.2 | 81.0 | 81.6 | 85.4 | 97.2 |
| Lomefloxacin HCl (Maxaquin) | 87.7 | 113.4 | 90.5 | 135.0 | 77.5 | 56.6 | 92.7 | 61.2 | 70.7 | 83.5 | 63.3 | 88.9 | 96.5 |
| Riboflavin (Vitamin B2) | 89.7 | 92.5 | 100.8 | 128.5 | 74.9 | 51.1 | 87.3 | 79.7 | 67.6 | 74.6 | 79.4 | 83.3 | 90.0 |
| Clomipramine HCl (Anafranil) | 88.9 | 119.1 | 115.6 | 167.6 | 60.2 | 47.5 | 70.5 | 46.2 | 69.1 | 75.7 | 75.8 | 87.1 | 82.7 |
| Ceftiofur hydrochloride | 92.8 | 114.2 | 91.9 | 92.2 | 69.4 | 44.0 | 85.5 | 50.6 | 61.6 | 159.3 | 73.1 | 85.0 | 92.2 |
| Tiotropium Bromide hydrate | 86.3 | 110.6 | 90.9 | 123.5 | 73.1 | 40.9 | 86.1 | 54.7 | 62.0 | 80.0 | 83.8 | 88.7 | 87.8 |
| Sulbactam sodium (Unasyn) | 101.2 | 109.4 | 87.6 | 87.4 | 73.5 | 40.6 | 74.7 | 48.8 | 65.9 | 73.5 | 74.5 | 80.6 | 97.2 |
| Terbinafine HCl (Lamisil) | 92.5 | 76.9 | 91.1 | 75.4 | 90.6 | 40.6 | 81.8 | 50.6 | 52.3 | 67.7 | 70.8 | 71.4 | 86.5 |
| Amoxicillin sodium (Amox) | 78.5 | 106.2 | 80.8 | 81.0 | 51.2 | 43.3 | 63.2 | 45.4 | 60.6 | 60.4 | 74.8 | 69.1 | 95.5 |
| Isoprenaline hydrochloride | 90.0 | 110.5 | 81.4 | 91.1 | 72.0 | 39.9 | 79.6 | 81.6 | 56.1 | 73.2 | 73.6 | 80.6 | 96.8 |
| Medroxyprogesterone acetate | 81.0 | 112.5 | 78.6 | 70.4 | 72.3 | 38.6 | 66.9 | 79.4 | 60.5 | 69.3 | 82.0 | 65.9 | 51.7 |
| Streptomycin sulfate | 77.5 | 114.5 | 84.5 | 88.9 | 65.5 | 40.6 | 68.7 | 23.3 | 57.3 | 72.0 | 59.1 | 46.6 | 93.3 |
| Tetracycline HCl | 74.1 | 114.8 | 74.1 | 96.1 | 88.2 | 41.1 | 55.9 | 34.1 | 72.8 | 75.9 | 42.9 | 71.8 | 93.7 |
| Xylometazoline HCl | 65.1 | 70.5 | 83.0 | 106.6 | 52.2 | 33.4 | 65.8 | 42.6 | 74.7 | 94.4 | 54.8 | 47.1 | 84.9 |
| Phenacetin | 54.1 | 65.6 | 72.5 | 57.2 | 40.4 | 39.1 | 75.1 | 23.3 | 34.4 | 62.7 | 40.4 | 48.5 | 95.3 |
| Trazodone HCl (Desyrel) | 54.4 | 92.1 | 85.1 | 86.7 | 43.4 | 39.7 | 78.1 | 52.1 | 34.1 | 69.2 | 49.6 | 56.4 | 90.8 |
| Brompheniramine | 101.7 | 101.9 | 95.7 | 111.0 | 121.1 | 83.0 | 85.8 | 97.9 | 109.3 | 75.8 | 96.9 | 98.9 | 121.5 |
| Clindamycin palmitate HCl | 92.3 | 85.7 | 108.4 | 66.7 | 43.0 | 67.7 | 84.1 | 92.4 | 128.3 | 87.6 | 100.7 | 93.5 | 93.3 |
| Acemetacin (Emflex) | 68.4 | 89.3 | 109.9 | 70.9 | 69.0 | 78.2 | 102.9 | 99.4 | 88.1 | 87.3 | 90.5 | 94.7 | 120.0 |
| Dabrafenib (GSK2118436) | 42.1 | 78.0 | 91.3 | 78.5 | 90.1 | 73.6 | 98.7 | 90.5 | 133.6 | 94.1 | 100.1 | 70.5 | 72.9 |
| Clindamycin | 55.6 | 86.7 | 96.5 | 75.5 | 86.2 | 63.3 | 58.8 | 67.2 | 127.7 | 86.0 | 111.7 | 92.4 | 144.7 |
| Paroxetine HCl | 31.9 | 37.7 | 65.8 | 42.1 | 21.5 | 44.1 | 49.2 | 56.4 | 80.1 | 56.4 | 70.6 | 53.8 | 79.1 |
| Zanamivir (Relenza) | 51.5 | 84.7 | 109.8 | 71.8 | 75.1 | 62.7 | 85.8 | 88.5 | 93.0 | 69.6 | 106.2 | 77.3 | 146.0 |
| Nithumic acid | 50.0 | 48.9 | 87.4 | 51.9 | 40.5 | 50.8 | 68.7 | 66.8 | 99.2 | 86.9 | 111.3 | 82.0 | 131.6 |
| Ciclopirox ethanolamine | 33.0 | 42.6 | 109.5 | 74.4 | 28.8 | 47.9 | 53.0 | 45.5 | 60.5 | 68.2 | 87.1 | 71.5 | 57.7 |
| Enrofloxacin | 65.2 | 75.8 | 77.2 | 67.0 | 94.5 | 44.5 | 37.4 | 77.9 | 67.5 | 66.6 | 48.6 | 84.8 | 86.6 |
| Medetomidine HCl | 59.7 | 70.4 | 91.9 | 78.4 | 107.8 | 49.8 | 37.4 | 104.5 | 73.7 | 72.3 | 65.6 | 79.4 | 84.5 |
| Diclofenac Potassium | 51.5 | 88.8 | 107.3 | 76.1 | 91.4 | 43.9 | 40.5 | 122.4 | 81.7 | 76.3 | 63.3 | 85.0 | 96.3 |
| Amikacin sulfate | 32.5 | 61.9 | 83.8 | 73.3 | 53.7 | 39.9 | 40.7 | 55.3 | 52.3 | 62.8 | 51.6 | 60.5 | 131.4 |
| Caspofungin acetate | 70.5 | 86.3 | 95.3 | 67.7 | 94.2 | 37.1 | 36.4 | 123.7 | 78.4 | 74.7 | 59.4 | 83.9 | 124.4 |
| Ulipristal | 48.2 | 88.2 | 69.0 | 72.4 | 55.4 | 40.3 | 36.1 | 55.8 | 59.9 | 65.4 | 49.3 | 67.8 | 93.8 |
| Indacaterol Maleate | 45.7 | 65.2 | 81.2 | 71.8 | 54.1 | 36.0 | 30.3 | 56.0 | 65.1 | 68.7 | 55.5 | 61.4 | 87.2 |
| Sulfathiazole | 30.8 | 50.9 | 65.7 | 47.7 | 54.6 | 38.8 | 30.8 | 54.5 | 47.2 | 60.1 | 94.9 | 78.1 | 96.7 |
| Amikacin hydrate | 87.7 | 77.0 | 88.4 | 96.3 | 85.8 | 87.7 | 104.5 | 138.3 | 111.0 | 81.4 | 101.8 | 99.0 | 108.2 |
| Trimethoprim | 83.6 | 92.0 | 102.5 | 89.0 | 97.7 | 108.1 | 73.6 | 92.4 | 125.3 | 104.5 | 150.8 | 98.7 | 96.8 |
| Biotin (Vitamin B7) | 71.3 | 76.1 | 100.6 | 90.7 | 103.5 | 94.2 | 85.1 | 93.5 | 86.4 | 89.1 | 131.8 | 99.2 | 85.2 |
| Sulfamerazine | 80.4 | 76.8 | 101.0 | 92.3 | 87.9 | 108.2 | 87.4 | 90.0 | 103.4 | 79.8 | 78.4 | 99.6 | 105.4 |
| Sodium salicylate | 74.9 | 73.5 | 84.3 | 94.4 | 82.1 | 90.1 | 77.9 | 136.8 | 107.4 | 89.0 | 87.9 | 102.0 | 94.7 |
| Methylthiouracil | 72.1 | 65.8 | 106.2 | 88.3 | 84.8 | 90.2 | 79.9 | 83.6 | 163.5 | 101.3 | 150.8 | 98.9 | 106.4 |
| Darifenacin HBr | 60.5 | 65.3 | 81.6 | 87.7 | 80.4 | 126.3 | 82.4 | 99.8 | 100.5 | 59.7 | 86.1 | 93.5 | 78.2 |
| Naftifine HCl | 63.3 | 57.5 | 91.2 | 80.6 | 104.0 | 72.3 | 58.5 | 79.6 | 127.0 | 84.5 | 108.6 | 86.3 | 93.2 |
| Sertaconazole nitrate | 52.0 | 53.9 | 77.4 | 58.9 | 97.1 | 96.3 | 69.5 | 89.4 | 75.4 | 76.4 | 77.2 | 94.9 | 73.4 |
| Benztropine mesylate | 67.5 | 62.0 | 86.0 | 95.3 | 83.0 | 91.7 | 89.4 | 101.3 | 68.2 | 63.3 | 75.3 | 81.4 | 81.1 |
| Abacavir sulfate | 57.2 | 46.2 | 82.6 | 84.2 | 97.1 | 67.0 | 94.6 | 147.6 | 87.0 | 79.6 | 76.0 | 100.5 | 107.5 |

TABLE 3-continued

The results of antibiotic drug for inhibiting cancer cell lines

| | | | | | | | | | |
|---|---|---|---|---|---|---|---|---|---|
| Ampicillin sodium | 68.9 | 45.7 | 76.1 | 75.2 | 105.0 | 53.5 | 77.9 | 72.0 | 102.6 | 99.1 | 98.1 | 88.9 | 103.8 |
| Antipyrine | 77.9 | 50.0 | 104.9 | 76.8 | 109.0 | 57.3 | 109.0 | 90.1 | 76.4 | 61.3 | 76.8 | 97.1 | 101.6 |
| Carbenicillin disodium | 70.2 | 45.4 | 88.9 | 77.8 | 62.9 | 76.2 | 84.3 | 84.3 | 53.5 | 59.0 | 84.4 | 86.2 | 113.8 |
| Amitriptyline HCl | 84.8 | 44.0 | 105.5 | 90.6 | 61.5 | 64.4 | 102.4 | 132.9 | 69.3 | 64.8 | 61.9 | 96.5 | 81.4 |
| Azatadine dimaleate | 40.7 | 30.2 | 84.5 | 72.2 | 67.1 | 48.5 | 83.4 | 78.5 | 123.1 | 79.7 | 104.3 | 95.7 | 112.6 |
| Triflusal | 95.9 | 90.9 | 102.7 | 104.8 | 93.3 | 81.3 | 133.8 | 86.5 | 112.5 | 97.8 | 87.5 | 102.6 | 93.3 |
| Clinafloxacin (PD127391) | 59.3 | 72.9 | 73.8 | 97.0 | 74.2 | 72.4 | 91.3 | 83.3 | 67.5 | 78.6 | 36.7 | 92.7 | 71.2 |
| Pentamidine | 38.2 | 47.3 | 76.4 | 55.9 | 50.6 | 65.8 | 86.3 | 59.3 | 51.8 | 68.5 | 33.2 | 74.4 | 57.8 |
| Pemirolast (BMY 26517) potassium | 70.8 | 54.7 | 82.1 | 88.4 | 69.4 | 81.8 | 100.7 | 93.7 | 82.9 | 83.2 | 53.8 | 107.4 | 101.1 |
| Homatropine Bromide | 41.2 | 61.6 | 70.7 | 79.0 | 25.2 | 67.2 | 76.8 | 52.2 | 63.8 | 70.2 | 38.4 | 86.5 | 96.5 |
| Colistin Sulfate | 36.1 | 74.6 | 77.7 | 84.3 | 26.1 | 62.2 | 92.4 | 36.2 | 97.6 | 66.7 | 41.4 | 92.0 | 108.9 |
| toltrazuril | 27.7 | 33.4 | 62.2 | 70.1 | 26.3 | 70.9 | 74.6 | 34.8 | 61.2 | 67.4 | 30.3 | 61.9 | 73.1 |
| Carbinnazole | 65.1 | 123.5 | 97.2 | 90.3 | 113.5 | 80.9 | 131.3 | 116.7 | 73.9 | 102.1 | 95.6 | 75.0 | 80.1 |
| Netilmicin Sulfate | 70.1 | 102.1 | 99.4 | 108.6 | 116.0 | 87.6 | 110.1 | 123.4 | 100.0 | 106.3 | 92.1 | 92.9 | 87.8 |
| Spironolactone | 61.0 | 99.5 | 90.5 | 117.6 | 96.6 | 79.8 | 117.0 | 90.1 | 67.5 | 87.7 | 88.5 | 67.2 | 57.2 |
| Ropivacaine HCl | 71.2 | 109.3 | 98.0 | 126.2 | 64.3 | 92.4 | 131.8 | 101.0 | 117.9 | 99.2 | 109.8 | 89.7 | 81.3 |
| Erythromycin Ethylsuccinate | 75.0 | 123.8 | 97.1 | 147.8 | 111.4 | 83.8 | 128.9 | 125.1 | 90.0 | 88.2 | 111.9 | 80.0 | 83.6 |
| Escitalopram oxalate | 68.0 | 98.4 | 94.0 | 95.0 | 62.3 | 80.4 | 115.5 | 80.6 | 122.0 | 97.4 | 79.5 | 91.6 | 92.7 |
| tinidazole | 60.6 | 71.6 | 95.5 | 97.8 | 104.4 | 91.1 | 100.5 | 111.7 | 79.5 | 88.0 | 85.6 | 78.5 | 89.0 |
| Pyrithione zinc | 27.1 | 39.6 | 70.4 | 47.4 | 35.4 | 60.6 | 57.4 | 28.7 | 29.7 | 51.8 | 24.3 | 45.5 | 34.5 |
| Mequinol | 63.8 | 86.0 | 95.6 | 87.1 | 57.2 | 67.5 | 102.8 | 97.0 | 118.0 | 74.4 | 68.0 | 85.2 | 112.2 |
| Spiramycin | 53.3 | 74.5 | 80.3 | 74.4 | 57.8 | 68.2 | 96.7 | 55.0 | 81.8 | 85.4 | 65.9 | 73.5 | 90.1 |
| Bismuth Subcitrate Potassium | 81.6 | 76.9 | 93.0 | 98.7 | 79.6 | 69.9 | 126.0 | 86.0 | 113.5 | 82.6 | 78.1 | 76.1 | 101.0 |
| Clofazimine | 37.3 | 41.4 | 82.2 | 59.3 | 64.2 | 74.4 | 53.1 | 51.7 | 49.5 | 51.2 | 53.2 | 68.3 | 85.0 |
| Dicloxacillin Sodium | 79.0 | 56.0 | 102.0 | 60.1 | 147.3 | 68.4 | 66.4 | 84.3 | 61.8 | 45.3 | 71.1 | 92.4 | 72.7 |
| Sulconazole Nitrate | 44.9 | 50.4 | 88.2 | 62.1 | 83.1 | 63.4 | 53.2 | 55.0 | 50.7 | 44.4 | 65.7 | 73.6 | 64.1 |
| Tilmicosin | 54.7 | 50.6 | 92.1 | 67.0 | 102.0 | 72.7 | 52.1 | 56.5 | 53.5 | 39.1 | 81.5 | 83.8 | 75.0 |
| Bacitracin | 54.7 | 53.2 | 86.4 | 68.4 | 61.4 | 65.4 | 46.9 | 68.3 | 51.4 | 41.4 | 70.0 | 69.9 | 85.9 |
| Azithromycin Dihydrate | 50.8 | 40.9 | 81.1 | 55.6 | 72.7 | 61.3 | 51.2 | 39.4 | 41.4 | 36.4 | 43.0 | 65.3 | 101.1 |
| Ampicillin Trihydrate | 53.7 | 52.2 | 92.4 | 59.3 | 95.3 | 63.6 | 56.3 | 61.3 | 41.9 | 36.5 | 65.3 | 78.4 | 92.7 |
| Orbifloxacin | 55.6 | 42.1 | 84.2 | 66.8 | 84.5 | 63.7 | 44.1 | 44.3 | 44.2 | 33.3 | 51.1 | 75.4 | 92.3 |
| Chlortetracycline HCl | 49.2 | 49.9 | 75.0 | 83.9 | 69.7 | 59.9 | 43.0 | 50.4 | 45.8 | 32.2 | 38.2 | 61.4 | 83.9 |
| Benzylpenicillin sodium | 51.7 | 56.4 | 86.4 | 57.1 | 54.8 | 57.1 | 43.1 | 39.6 | 36.4 | 31.3 | 36.1 | 62.8 | 86.7 |
| Chlorpropamide | 62.1 | 35.9 | 92.5 | 59.9 | 51.2 | 55.8 | 42.7 | 59.1 | 36.9 | 32.5 | 44.4 | 59.3 | 96.7 |
| Cetylpyridinium Chloride | 35.6 | 33.6 | 60.9 | 37.1 | 33.4 | 48.7 | 47.4 | 37.2 | 29.2 | 40.9 | 37.1 | 50.7 | 30.8 |
| Sulfaguanidine | 144.7 | 91.1 | 96.1 | 113.2 | 84.0 | 95.6 | 83.5 | 107.1 | 82.2 | 92.6 | 85.9 | 78.9 | 99.1 |
| Climbazole | 70.6 | 54.7 | 94.4 | 94.0 | 93.3 | 84.2 | 97.7 | 102.3 | 72.7 | 100.8 | 99.6 | 101.0 | 111.3 |
| Mezlocillin Sodium | 106.9 | 75.3 | 95.1 | 111.2 | 72.2 | 81.0 | 92.9 | 91.9 | 78.0 | 100.6 | 97.8 | 115.5 | 91.4 |
| Nifuroxazide | 51.6 | 42.0 | 73.0 | 66.6 | 36.7 | 57.6 | 51.0 | 56.2 | 33.2 | 80.1 | 92.0 | 58.3 | 38.8 |
| Paromomycin Sulfate | 91.4 | 84.5 | 101.1 | 96.2 | 80.2 | 99.0 | 92.1 | 106.2 | 78.2 | 112.3 | 146.4 | 67.1 | 87.1 |
| Penciclovir | 64.2 | 62.2 | 95.7 | 81.7 | 71.0 | 71.5 | 98.5 | 79.1 | 74.7 | 110.3 | 106.2 | 98.5 | 113.7 |
| Domiphen Bromide | 36.3 | 34.0 | 62.1 | 38.0 | 32.5 | 46.5 | 44.4 | 37.3 | 28.7 | 31.3 | 38.9 | 48.7 | 30.0 |
| Salicylanilide | 92.8 | 70.4 | 97.2 | 117.7 | 77.8 | 80.5 | 83.5 | 108.2 | 62.1 | 106.4 | 89.7 | 86.2 | 71.1 |
| Betamipron | 85.8 | 56.7 | 90.9 | 75.9 | 75.2 | 72.8 | 88.2 | 85.4 | 72.3 | 117.6 | 92.6 | 93.5 | 96.2 |
| Chlorquinaldol | 43.0 | 34.5 | 82.3 | 42.6 | 35.7 | 59.6 | 75.4 | 70.5 | 54.5 | 47.8 | 68.4 | 62.8 | 64.8 |
| Ethacridine lactate monohydrate | 40.1 | 38.9 | 65.5 | 39.9 | 38.2 | 52.5 | 49.7 | 46.8 | 75.1 | 68.7 | 64.6 | 50.1 | 44.1 |
| Aminothiazole | 78.4 | 59.9 | 90.4 | 65.7 | 62.3 | 68.7 | 101.2 | 86.0 | 56.1 | 108.4 | 93.8 | 86.4 | 120.8 |

TABLE 3-continued

The results of antibiotic drug for inhibiting cancer cell lines

| | A375 | HCT116(WT) | HepG2 | HeLa | AGS | H1650 | MKN-45 | TSGH | A549 | MCF7 | PC3 | LoVo | HL-60 |
|---|---|---|---|---|---|---|---|---|---|---|---|---|---|
| Florfenicol | 88.4 | 99.0 | 161.3 | 95.1 | 100.6 | 87.0 | 117.4 | 86.9 | 67.8 | 122.6 | 101.7 | 92.9 | 109.3 |
| Furaltadone HCl | 66.0 | 66.0 | 83.2 | 64.0 | 68.2 | 83.1 | 72.6 | 81.3 | 67.9 | 102.8 | 99.2 | 62.2 | 64.6 |
| Dirithromycin | 83.7 | 85.3 | 90.6 | 91.9 | 63.2 | 65.5 | 106.3 | 77.2 | 64.8 | 62.6 | 77.1 | 83.7 | 90.2 |
| Valnemulin HCl | 57.1 | 95.8 | 126.1 | 116.6 | 75.5 | 78.8 | 91.4 | 66.9 | 62.2 | 66.7 | 83.4 | 73.6 | 93.3 |
| Piperacillin Sodium | 67.9 | 91.8 | 96.3 | 91.8 | 98.3 | 71.6 | 87.1 | 91.4 | 37.1 | 52.3 | 79.3 | 97.4 | 108.1 |
| Minocycline HCl | 81.6 | 105.2 | 103.3 | 101.1 | 87.6 | 74.0 | 95.0 | 60.4 | 42.5 | 49.9 | 53.8 | 87.3 | 68.1 |
| Fidaxomicin | 70.3 | 101.8 | 99.6 | 82.2 | 94.9 | 61.2 | 94.2 | 82.4 | 40.6 | 46.6 | 59.4 | 89.6 | 99.2 |
| Primaquine Diphosphate | 44.6 | 69.5 | 81.4 | 55.0 | 43.9 | 56.4 | 64.3 | 55.5 | 31.4 | 36.7 | 60.3 | 72.6 | 34.1 |
| Cetrimonium Bromide | 36.1 | 62.3 | 62.8 | 42.6 | 42.4 | 54.6 | 61.5 | 34.8 | 25.0 | 36.4 | 38.7 | 55.4 | 27.9 |
| Carbadox | 52.4 | 72.8 | 88.7 | 60.0 | 51.9 | 56.9 | 104.1 | 67.9 | 24.8 | 34.6 | 52.5 | 54.4 | 87.0 |
| Ceftazidime Pentahydrate | 87.7 | 89.5 | 93.6 | 70.0 | 53.5 | 58.5 | 94.6 | 78.7 | 26.7 | 35.5 | 38.5 | 72.5 | 89.3 |
| Clinafoxacin HCl | 46.4 | 96.1 | 74.8 | 56.5 | 48.1 | 59.8 | 66.9 | 80.5 | 33.5 | 34.3 | 38.4 | 54.1 | 85.9 |
| Colistimethate Sodium | 48.2 | 61.9 | 64.5 | 42.9 | 43.0 | 55.7 | 62.7 | 33.7 | 25.4 | 37.1 | 39.6 | 57.5 | 94.0 |
| Meclocycline Sulfosalicylate | 92.8 | 99.5 | 94.4 | 90.6 | 88.1 | 92.2 | 140.8 | 44.2 | 62.1 | 95.0 | 77.6 | 101.1 | 81.3 |
| Moxalactam Disodium | 80.8 | 73.9 | 79.1 | 61.3 | 76.9 | 66.9 | 110.5 | 55.9 | 76.6 | 80.7 | 95.0 | 94.0 | 100.8 |
| Piromidic Acid | 86.7 | 89.8 | 73.8 | 95.5 | 85.9 | 67.2 | 100.1 | 90.5 | 80.5 | 99.5 | 107.1 | 95.2 | 95.2 |
| Rolitetracycline | 82.5 | 67.7 | 71.2 | 53.9 | 61.1 | 113.1 | 95.7 | 54.3 | 111.6 | 88.8 | 105.0 | 86.1 | 101.8 |
| Thiostrepton | 27.6 | 35.6 | 49.2 | 37.8 | 25.7 | 45.4 | 56.7 | 20.1 | 62.2 | 65.0 | 55.7 | 52.9 | 37.8 |
| Thonzonium Bromide | 24.4 | 32.9 | 45.1 | 28.0 | 22.5 | 36.7 | 47.0 | 18.4 | 36.6 | 47.0 | 46.2 | 39.4 | 35.2 |
| Cinoxacin | 68.3 | 66.2 | 69.7 | 64.0 | 83.2 | 67.1 | 98.9 | 71.5 | 74.2 | 74.9 | 87.0 | 97.0 | 108.9 |
| Bekanamycin | 55.5 | 73.6 | 85.3 | 95.2 | 81.7 | 80.8 | 74.5 | 76.2 | 58.3 | 57.5 | 76.3 | 96.9 | 96.8 |
| Difloxacin HCl | 58.5 | 96.7 | 71.2 | 130.0 | 82.9 | 77.5 | 79.4 | 52.0 | 64.5 | 57.5 | 77.3 | 95.7 | 77.0 |
| Cephapirin Sodium | 50.2 | 65.8 | 79.8 | 69.2 | 79.8 | 76.2 | 69.1 | 78.2 | 57.7 | 52.3 | 82.3 | 92.8 | 84.3 |
| Clofoctol | 34.5 | 61.0 | 77.9 | 58.0 | 86.7 | 77.0 | 73.6 | 72.3 | 55.6 | 49.5 | 63.4 | 74.7 | 83.0 |
| Pasiniazid | 38.8 | 79.9 | 60.2 | 70.5 | 52.8 | 69.8 | 49.5 | 47.8 | 40.1 | 44.7 | 65.6 | 56.5 | 113.2 |
| Curcumin | 104.1517 | 93.59955 | 98.32845 | 66.17249 | 72.20966 | 74.6574 | 46.36867 | 95.41959 | 104.8165 | 61.78115 | 77.8638 | 80.01025 | 111.3333 |
| Talc | 66.78463 | 97.48187 | 124.542 | 80.03129 | 86.17534 | 88.30275 | 63.44364 | 91.07906 | 52.4318 | 47.10155 | 45.60222 | 74.11115 | 99.89936 |
| Avobenzone (Parsol 1789) | 62.58342 | 87.88148 | 111.1525 | 65.6383 | 76.38487 | 80.51988 | 61.16856 | 96.26068 | 52.13581 | 54.1091 | 42.88069 | 84.24497 | 86.01705 |
| Meglumine | 78.19291 | 92.70295 | 90.78556 | 74.0779 | 95.03349 | 61.97811 | 74.64493 | 109.0826 | 107.6122 | 97.02401 | 76.80619 | 78.35011 | 114.1135 |
| Geniposide | 73.42172 | 73.92127 | 88.5582 | 80.99412 | 54.16912 | 71.18227 | 45.62227 | 53.10121 | 63.66648 | 73.82923 | 65.54175 | 74.10151 | 119.651 |
| Genipin | 78.03728 | 82.7025 | 87.05908 | 74.51176 | 49.56541 | 69.45813 | 54.06743 | 67.65546 | 61.77802 | 71.66373 | 71.60605 | 74.63694 | 116.7718 |
| Benzoic acid | 36.9762 | 41.89746 | 79.12599 | 59.59074 | 53.05571 | 57.24681 | 43.37741 | 39.47556 | 36.71191 | 31.36544 | 36.78594 | 60.4637 | 110.8349 |
| Coumarin | 156.6911 | 93.73406 | 100.212 | 96.54225 | 98.51982 | 95.62174 | 101.0172 | 107.874 | 91.82918 | 100.5157 | 86.27522 | 88.27368 | 102.1924 |
| Choline Chloride | 132.0856 | 103.8256 | 102.9483 | 103.0871 | 97.08145 | 90.17561 | 99.25918 | 128.9261 | 96.0435 | 107.7357 | 106.291 | 76.68864 | 91.11496 |
| 1-Hexadecanol | 112.5688 | 69.79481 | 95.95113 | 91.32686 | 89.43803 | 84.34979 | 85.45997 | 101.1905 | 83.97244 | 101.2146 | 91.9098 | 98.76884 | 92.1751 |
| Sodium Gluconate | 115.9939 | 89.09112 | 95.30493 | 72.9899 | 90.82623 | 94.61319 | 93.00088 | 97.38626 | 91.87137 | 94.7031 | 78.05738 | 100 | 91.17986 |
| Trometamol | 125.5535 | 90.41271 | 96.65792 | 90.91781 | 78.14852 | 95.40816 | 88.29058 | 102.4825 | 79.48622 | 98.80952 | 97.0034 | 67.96286 | 91.28804 |
| Uracil | 98.2263 | 94.33689 | 100.1716 | 106.5128 | 82.94865 | 91.82487 | 100.0951 | 104.0354 | 80.53628 | 103.1618 | 162.9771 | 70.22336 | 98.69465 |
| Bemegride | 62.66055 | 47.66404 | 90.69063 | 62.71891 | 61.96688 | 69.89796 | 99.65723 | 93.29615 | 60.70692 | 123.2745 | 112.8373 | 88.48897 | 124.8233 |
| Isosorbide | 53.49235 | 55.08927 | 90.09491 | 72.77899 | 69.04165 | 73.30327 | 93.12251 | 77.46063 | 60.70692 | 78.62927 | 94.34111 | 81.75457 | 125.0541 |
| Dibenzothiophene | 70.59939 | 52.65476 | 89.09532 | 94.58648 | 59.24068 | 76.0916 | 92.06103 | 88.1671 | 62.3289 | 71.42857 | 80.23341 | 79.70936 | 110.1183 |
| Sucralose | 65.36391 | 61.71458 | 98.55618 | 96.30577 | 80.13169 | 91.5401 | 101.1499 | 113.2437 | 80.14251 | 64.1604 | 129.6864 | 62.02234 | 96.39406 |
| Benzbromarone | 83.29052 | 54.79365 | 95.26454 | 77.9049 | 66.70848 | 72.0337 | 94.09553 | 94.33508 | 74.32965 | 78.62927 | 78.84756 | 73.77557 | 88.54031 |
| Nithiamide | 99.17644 | 128.4237 | 102.8409 | 104.2825 | 80.13169 | 75.3432 | 86.22105 | 99.91064 | 51.50565 | 71.17313 | 80.89452 | 105.4056 | 85.47609 |
| Alexidine HCl | 96.71824 | 86.86044 | 94.76461 | 82.98817 | 102.2262 | 67.09287 | 76.70771 | 121.5449 | 39.25136 | 65.52619 | 74.45062 | 89.83966 | 102.4575 |
| 9-Aminoacridine | 38.08335 | 65.83932 | 65.92938 | 44.85207 | 45.05644 | 57.52355 | 64.40926 | 36.61636 | 25.29486 | 34.82775 | 38.04292 | 54.64359 | 29.4161 |
| | 36.38008 | 70.50947 | 63.45373 | 43.57249 | 42.76756 | 56.94482 | 63.10466 | 34.63066 | 25.8051 | 34.12577 | 38.65047 | 58.52516 | 28.83353 |

TABLE 3-continued

The results of antibiotic drug for inhibiting cancer cell lines

| | | | | | | | | | | |
|---|---|---|---|---|---|---|---|---|---|---|
| Calcium Gluceptate | 36.96656 | 74.09101 | 76.87703 | 43.92751 | 79.67182 | 54.25303 | 74.23043 | 33.80659 | 24.91426 | 34.24375 | 37.91365 | 55.29449 | 113.4525 |
| Clopamide | 63.10207 | 101.9268 | 92.847 | 87.0784 | 50.28219 | 53.97039 | 89.43125 | 58.96545 | 32.42576 | 33.3589 | 40.32446 | 54.32608 | 102.2231 |

Repeated Experiment

According to the listing antibiotic drug inhibit cancer cell growth results of Table 3, the inventors take the repeat experiment for checking effectively the inhibitory effect of cancer cell growth by the antibiotic drug. The results show as Table. 4.

TABLE 4

The results of antibiotic drug inhibiting cancer cell lines

| | AGS | MKN-45 | A549 | H1650 | TSGH-8301 | T24 | HepG2 | Hep3B | HCT116 | LoVo | HeLa | C-33A |
|---|---|---|---|---|---|---|---|---|---|---|---|---|
| paroxetine | 12.16 | 40.49 | 92.43 | 56.85 | 38.35 | 99.95 | 54.13 | 66.07 | 28.38 | 57.97 | 63.82 | 33.19 |
| Cetrimonium Bromide | 20.83 | 35.25 | 20.71 | 40.26 | 22.33 | 19.1 | 56.6 | 58.68 | 19.31 | 51.72 | 20.73 | 35.29 |
| Thonzonium Bromide | 14.37 | 31.18 | 15 | 37.63 | 16.72 | 18.47 | 47.73 | 51.26 | 18.75 | 50.9 | 20.28 | 32.48 |
| Olanzapine (Zyprexa) | 121.8 | 125.4 | 105.8 | 106.8 | 151.6 | 110.1 | 114.1 | 132.4 | 124.1 | 81.37 | 121.2 | 98.19 |
| Clomipramine hydrochloride (Anafranil) | 122.1 | 125.3 | 86.37 | 103.2 | 139.2 | 109.4 | 106.4 | 135.1 | 137.2 | 65.67 | 113 | 117.7 |
| Amitriptyline HCl | 146 | 134.6 | 73.34 | 111.1 | 157.1 | 97.45 | 105.5 | 123.9 | 107.7 | 90.47 | 111.2 | 100.2 |
| Escitalopram oxalate | 145.1 | 127.1 | 102.8 | 92.11 | 134.6 | 97.65 | 113.2 | 133.8 | 122.9 | 89.35 | 125.5 | 110.1 |
| Ritonavir | 96.25 | 95.79 | 72.66 | 78.24 | 115.3 | 97.34 | 85.48 | 101.8 | 83.57 | 90.21 | 86.09 | 111 |
| Entecavir hydrate | 88.67 | 92.54 | 104 | 84.11 | 103.4 | 96.39 | 88.91 | 90.77 | 99.92 | 96.66 | 76.9 | 96.67 |
| Posaconazole | 65.68 | 92.77 | 18.12 | 67.54 | 81.89 | 55.37 | 57.82 | 95.24 | 51.57 | 61.96 | 49.41 | 35.51 |
| Ivermectin | 79.82 | 102.1 | 33.35 | 50.2 | 63.74 | 101.7 | 65.3 | 63.22 | 62.7 | 53.26 | 58.86 | 85.05 |
| Tigecycline | 90.64 | 114 | 91.48 | 66.93 | 112.7 | 109.1 | 97.2 | 105.5 | 89.69 | 96.03 | 102 | 99.98 |
| Linezolid (Zyvox) | 104.4 | 136.9 | 82.14 | 95.64 | 99.71 | 1141 | 107.3 | 99.88 | 107.3 | 89.47 | 89.19 | 132.2 |
| Telaprevir (VX-950) | 111 | 107.4 | 80.36 | 107.3 | 103.2 | 114.7 | 114 | 121 | 93.64 | 87.03 | 92.58 | 102.5 |
| Saxagliptin (BMS-477118, Onglyza) | 121.3 | 117.7 | 98.68 | 101.5 | 119.6 | 90.82 | 118 | 122.9 | 106.8 | 82.99 | 114.7 | 104.4 |
| Nitazoxanide (Alinia, Annita) | 99.04 | 97.28 | 95.57 | 85.86 | 87.18 | 76.47 | 107.5 | 106.8 | 98.42 | 94.76 | 84.93 | 103.9 |
| Amprenavir (Agenerase) | 98.57 | 102.7 | 79.88 | 88.12 | 96.1 | 90.55 | 94.54 | 95.2 | 94.49 | 95.49 | 67.87 | 108.6 |
| Albendazole (Albenza) | 29.46 | 62.34 | 24.2 | 41.75 | 46.61 | 37.98 | 62.7 | 61.38 | 20.91 | 50.79 | 29.9 | 42.62 |
| Nitrofurazone (Nitrofural) | 88.25 | 86.77 | 113.8 | 67.33 | 83.88 | 87.38 | 95.44 | 95.27 | 110.4 | 84.8 | 51.16 | 83.2 |
| Adefovir Dipivoxil (Preveon, Hepsera) | 78.05 | 86.57 | 76.71 | 54.04 | 69.95 | 44.75 | 80.14 | 71.53 | 55.44 | 58.12 | 77.42 | 68.03 |
| Rifapentine (Priftin) | 76.38 | 98.6 | 87.37 | 68.97 | 94.71 | 86.32 | 112.1 | 110.1 | 100.7 | 93.47 | 104.4 | 91.74 |
| Trifluridine (Viroptic) | 83.23 | 89.49 | 61.63 | 77.96 | 86.44 | 55.36 | 85.57 | 77.6 | 51.5 | 62.52 | 86.89 | 66.53 |
| Rifaximin (Xifaxan) | 98.11 | 93.54 | 107.7 | 69.54 | 114.5 | 96.76 | 115.4 | 110.4 | 100.8 | 80.33 | 106 | 107.4 |
| Oxfendazole | 51.41 | 79.88 | 64.67 | 63.95 | 67.58 | 70.17 | 99.38 | 106.8 | 67.39 | 73.69 | 36.97 | 86.44 |
| Albendazole Oxide (Ricobendazole) | 80.02 | 74.3 | 95.47 | 64.6 | 63.26 | 89.78 | 92.92 | 97.94 | 91.27 | 88.16 | 49.41 | 101.5 |
| Flubendazole (Flutelmium) | 28.25 | 63.06 | 22.71 | 35.69 | 45.64 | 34.67 | 56.8 | 56.93 | 20.63 | 53.35 | 25.78 | 46.4 |
| Oxibendazole | 37.57 | 65.63 | 23.97 | 41.26 | 48.57 | 38.06 | 64.49 | 59.82 | 22.07 | 53.38 | 29.28 | 47.75 |
| Metronidazole (Flagyl) | 113.3 | 107.8 | 97.65 | 87.17 | 92.37 | 93.83 | 94.06 | 92.33 | 98.93 | 118.5 | 75.35 | 113.7 |
| Tioconazole | 119.9 | 99.88 | 100.5 | 90.33 | 105.2 | 88.81 | 109.2 | 120.1 | 102.8 | 99.79 | 96.87 | 114.4 |
| Sulfisoxazole | 108.5 | 104.7 | 104.7 | 75.91 | 104.6 | 90.67 | 122.1 | 110 | 97.9 | 112.5 | 120.2 | 115.8 |
| Nystatin (Mycostatin) | 115 | 95.89 | 94.3 | 72.42 | 91.24 | 76.44 | 101.6 | 108.8 | 103 | 102.5 | 108.2 | 105.3 |
| Levamisole Hydrochloride (Ergamisol) | 120.5 | 112.3 | 104.9 | 78.34 | 106.8 | 92.87 | 127.7 | 121.1 | 116 | 100.7 | 137 | 96.19 |
| Miconazole nitrate | 113.7 | 99.81 | 97.27 | 83.13 | 102.3 | 77.7 | 108.3 | 126.1 | 121.5 | 81.28 | 95.73 | 117.1 |
| Ammonium Glycyrrhizinate (AMGZ) | 109.2 | 96.41 | 83.55 | 76.88 | 105.2 | 107.9 | 119.7 | 102.1 | 93.44 | 100.4 | 103.4 | 108.4 |
| Amfebutamone (Bupropion) | 116.9 | 103.1 | 69.1 | 95.97 | 115.8 | 99.6 | 92.33 | 82.09 | 78.27 | 114.6 | 84.46 | 106.9 |
| Loperamide hydrochloride | 22.18 | 61.54 | 26.25 | 41.28 | 42.91 | 73.49 | 35.76 | 50.16 | 47.26 | 49.29 | 36.83 | 39.63 |
| Mycophenolic (Mycophenolate) | 31.68 | 64.94 | 38.97 | 54.54 | 57.45 | 48.23 | 62.08 | 66.83 | 43.07 | 58.58 | 46.1 | 51.84 |
| Cloxacillin sodium (Cloxacap) | 140.1 | 111.3 | 98.33 | 86.43 | 136.6 | 100.9 | 131 | 118.4 | 115.2 | 98.38 | 120.1 | 104.6 |
| Amoxicillin sodium (Amox) | 128.2 | 110.7 | 101 | 87.81 | 129.6 | 105.9 | 124.5 | 109.8 | 112.2 | 103.3 | 112.6 | 108.2 |
| Tetracycline HCl | 93.99 | 133 | 99.68 | 87.12 | 102.6 | 130.2 | 106.3 | 92.23 | 114.1 | 92.04 | 78.95 | 102.9 |
| Vancomycin HCl (Vancocin) | 108.9 | 116.9 | 86.65 | 82.92 | 118 | 95.32 | 92.06 | 94.6 | 94.76 | 101 | 78.82 | 100.6 |
| Xylometazoline HCl | 125.1 | 120.7 | 83.01 | 95.35 | 121.9 | 92.52 | 106.1 | 114 | 101.4 | 88.73 | 117.3 | 103.6 |
| Phenacetin | 121.7 | 122.7 | 87.62 | 90.09 | 128 | 101 | 121.1 | 106.2 | 102.4 | 87.66 | 109.9 | 113.6 |
| Trazodone hydrochloride (Desyrel) | 120.4 | 108.2 | 92.03 | 82.39 | 133.7 | 105.5 | 108.6 | 109.5 | 113.3 | 88.78 | 105.3 | 112.2 |
| Thiamphenicol (Thiophenicol) | 140.3 | 177 | 97.41 | 94.92 | 136.8 | 164 | 143.9 | 103.3 | 150 | 96.08 | 90.82 | 140.2 |
| Ciclopirox ethanolamine | 36.59 | 72.97 | 23.67 | 53.76 | 43.63 | 41.2 | 102.4 | 48.66 | 29.52 | 65.53 | 41.02 | 42.12 |
| Niclosamide (Niclocide) | 23.05 | 50.74 | 16.68 | 36.77 | 35.94 | 26.49 | 37.55 | 60.79 | 23.91 | 41.95 | 25.4 | 39.49 |
| Etravirine (TMC125) | 49.66 | 62.38 | 37 | 51.13 | 56.13 | 56.73 | 68.31 | 78.35 | 54.08 | 45.66 | 47.73 | 63.88 |
| Indacaterol Maleate | 50.2 | 84.53 | 79.64 | 86.56 | 101.4 | 122 | 84.41 | 97.64 | 91.94 | 79.12 | 96.62 | 94.35 |
| Pentamidine | 92.36 | 97.29 | 35.42 | 68.55 | 82.65 | 122.8 | 69.12 | 72.02 | 100.5 | 63.36 | 44.6 | 65.68 |

TABLE 4-continued

The results of antibiotic drug inhibiting cancer cell lines

| | | | | | | | | | | | | |
|---|---|---|---|---|---|---|---|---|---|---|---|---|
| Clofazimine | 78.77 | 107.8 | 87.1 | 92.17 | 110.6 | 74.06 | 90.41 | 91.61 | 82.94 | 83.4 | 94.34 | 111.4 |
| Azithromycin Dihydrate | 77.25 | 95.84 | 66.29 | 98.63 | 118.6 | 111.5 | 91.4 | 109.1 | 80.71 | 79.22 | 105.4 | 92.62 |
| Chlortetracycline HCl | 99.94 | 142.1 | 99.29 | 88.54 | 152.5 | 122.1 | 112.6 | 117.2 | 91.53 | 74.36 | 83.96 | 88.03 |
| Benzylpenicillin sodium | 110.3 | 123.7 | 97.21 | 121.3 | 131.3 | 107.9 | 108.4 | 112.9 | 93.95 | 78.27 | 106.9 | 109.6 |
| Chlorquinaldol | 53.88 | 92.37 | 37.8 | 75.19 | 86.98 | 50.57 | 81.99 | 105.1 | 38.51 | 45.8 | 64.94 | 47.46 |
| Primaquine Diphosphate | 37.08 | 63.06 | 47.37 | 66.76 | 51.51 | 72.63 | 81.04 | 115.2 | 60.94 | 81.19 | 61.17 | 96.76 |
| Colistimethate Sodium | 87.05 | 104.8 | 89.46 | 82.62 | 111.7 | 108.3 | 107.4 | 102.2 | 86.11 | 85.06 | 77.79 | 107.5 |
| Clofoctol | 83.89 | 117 | 90.58 | 69.57 | 109.3 | 90.83 | 113.7 | 135.4 | 76.64 | 67.1 | 98.02 | 116.7 |
| Rosuvastatin calcium (Crestor) | 104.4 | 109.9 | 95.1 | 76.74 | 112.6 | 75.94 | 108 | 109.3 | 85.62 | 103.1 | 97.1 | 100.8 |
| Mevastatin | 71.25 | 92.72 | 101.3 | 69.43 | 94.4 | 67.51 | 98.7 | 97.65 | 73.63 | 90.48 | 90.53 | 101.6 |

| | PC-3 | MCF-7 | MDA-MB231 | NIH-OVCAR-3 | TOV-21G | AsPC-1 | BxPC-3 | SAS | U2OS | A375 | BCC | 786-O |
|---|---|---|---|---|---|---|---|---|---|---|---|---|
| paroxetine | 44.06 | 51.17 | 41.76 | 85.96 | 87.12 | 76.98 | 77.74 | 51.5 | 33.19 | 43.83 | 58.23 | 24.02 |
| Cetrimonium Bromide | 28.53 | 47.47 | 33.73 | 56.47 | 15.69 | 30.03 | 25.89 | 21.73 | 36.44 | 12.93 | 23.59 | 16.85 |
| Thonzonium Bromide | 29.26 | 41.03 | 33.11 | 55.67 | 17.42 | 27.56 | 24.44 | 20.45 | 31.69 | 12.36 | 23.45 | 16.75 |
| Olanzapine (Zyprexa) | 112.8 | 86.77 | 111.1 | 96.85 | 105 | 84.25 | 65.94 | 59.27 | 65.96 | 98.29 | 100.7 | 91.78 |
| Clomipramine hydrochloride (Anafranil) | 91.19 | 65.87 | 117.1 | 100.6 | 118.2 | 77.17 | 78.33 | 51.61 | 58.43 | 100.9 | 124.3 | 80.31 |
| Amitriptyline HCl | 99.38 | 67.66 | 105.9 | 103.5 | 117.5 | 73.08 | 67.15 | 67.55 | 68.5 | 94.3 | 112.8 | 85.52 |
| Escitalopram oxalate | 120.1 | 80.08 | 110.7 | 100.9 | 117.4 | 80.26 | 68.08 | 65.27 | 62.23 | 100.8 | 102.5 | 88.82 |
| Ritonavir | 92.69 | 67.01 | 102.1 | 92.21 | 72.73 | 88.64 | 89.57 | 73.17 | 87.1 | 80.26 | 86.4 | 102.5 |
| Entecavir hydrate | 118.3 | 92.93 | 98.9 | 108.6 | 85.54 | 98.43 | 97.15 | 74.57 | 85.34 | 89.05 | 69.5 | 92.66 |
| Posaconazole | 52.06 | 48.04 | 60.36 | 62.31 | 37.26 | 32.16 | 42.56 | 26.65 | 38.87 | 47.91 | 43.55 | 18.14 |
| Ivermectin | 27.87 | 48.13 | 83.03 | 61.85 | 42.41 | 41.75 | 65.76 | 41.52 | 50.69 | 44.36 | 33.64 | 55.69 |
| Tigecycline | 112 | 79.12 | 93.36 | 91.12 | 67.14 | 86.48 | 75.56 | 66.21 | 83.95 | 83.22 | 79.89 | 100.5 |
| Linezolid (Zyvox) | 115.3 | 73.07 | 96.16 | 109.6 | 78.16 | 92.58 | 95.64 | 83.98 | 99.83 | 82.8 | 67.21 | 98.62 |
| Telaprevir (VX-950) | 89.23 | 76.39 | 95.57 | 95.59 | 81.61 | 69.3 | 63.89 | 67.61 | 63.41 | 105.2 | 92.5 | 94.85 |
| Saxagliptin (BMS-477118, Onglyza) | 112 | 83.97 | 102 | 114.2 | 91.41 | 75.97 | 83.75 | 62.71 | 62.9 | 111.4 | 88.11 | 98.33 |
| Nitazoxanide (Alinia, Annita) | 90.27 | 79.28 | 91.23 | 104.5 | 62.56 | 84.09 | 89.5 | 78.89 | 83.33 | 94.2 | 76 | 44.2 |
| Amprenavir (Agenerase) | 87.44 | 68.35 | 83.45 | 105.9 | 96.99 | 90.4 | 74.63 | 83.28 | 101.1 | 88.08 | 74.5 | 96.74 |
| Albendazole (Albenza) | 37.99 | 69.83 | 44.52 | 52.49 | 29.79 | 35.28 | 36.62 | 36.08 | 50.07 | 36.21 | 31.25 | 21.55 |
| Nitrofurazone (Nitrofural) | 98.64 | 106.6 | 83.95 | 99.51 | 95.65 | 76.69 | 71.62 | 92.3 | 92.43 | 94.69 | 92.98 | 89.97 |
| Adefovir Dipivoxil (Preveon, Hepsera) | 74.85 | 75.5 | 71.86 | 78.82 | 77.26 | 48.67 | 56.92 | 40.03 | 68.48 | 37.74 | 38.85 | 25.95 |
| Rifapentine (Priftin) | 98.43 | 84.1 | 93.34 | 104.1 | 79.65 | 78.22 | 73.95 | 85.36 | 87.2 | 98.17 | 85.71 | 85.92 |
| Trifluridine (Viroptic) | 101.2 | 79.64 | 75.06 | 105.1 | 81.44 | 62.13 | 73.12 | 33.49 | 61.22 | 59.44 | 83.3 | 37.87 |
| Rifaximin (Xifaxan) | 95.28 | 89.94 | 98.66 | 100.1 | 87.95 | 71.17 | 88.5 | 69.8 | 72.88 | 98.24 | 81.83 | 87.56 |
| Oxfendazole | 72.72 | 64.63 | 73.93 | 62.17 | 65.1 | 50.85 | 54.96 | 72.33 | 83.4 | 59.67 | 55.28 | 72.33 |
| Albendazole Oxide (Ricobendazole) | 78.73 | 68.26 | 81.12 | 72.07 | 76.35 | 67.6 | 50.24 | 92.4 | 84.78 | 66.51 | 57.15 | 86.08 |
| Flubendazole (Flutelmium) | 32.11 | 55.01 | 43.43 | 59.15 | 24.84 | 35.53 | 32.76 | 45.16 | 48.74 | 30.32 | 31.79 | 20.97 |
| Oxibendazole | 38.91 | 60.91 | 48.93 | 54.83 | 26.64 | 32.96 | 29.09 | 41.22 | 46.65 | 31.81 | 34.31 | 18.51 |
| Metronidazole (Flagyl) | 95.57 | 77.27 | 93.29 | 109.5 | 95.83 | 83.06 | 83.62 | 112.5 | 99.63 | 74.71 | 68.23 | 92.02 |
| Tioconazole | 103.6 | 97.81 | 103.1 | 92.55 | 78.52 | 80.07 | 69.23 | 93.62 | 92.4 | 97.82 | 87.75 | 75.56 |
| Sulfisoxazole | 110.6 | 106.2 | 104.1 | 108.2 | 84.49 | 80.08 | 67.12 | 101.1 | 88.64 | 106.6 | 102.3 | 93.27 |
| Nystatin (Mycostatin) | 109.1 | 89.88 | 86.09 | 108.3 | 74.99 | 75.83 | 69.94 | 97.09 | 76.11 | 99.37 | 92.4 | 89.48 |
| Levamisole Hydrochloride (Ergamisol) | 125.7 | 102.4 | 102.7 | 105.6 | 83.45 | 85.72 | 68.02 | 89.56 | 79.87 | 113.9 | 114.1 | 93.24 |
| Miconazole nitrate | 115.7 | 95.64 | 106.6 | 94.77 | 80.62 | 75.5 | 65.27 | 69.58 | 64.24 | 100.3 | 80.67 | 75.24 |
| Ammonium Glycyrrhizinate (AMGZ) | 120.7 | 69.06 | 98.74 | 101 | 74.39 | 100.6 | 102.8 | 83.22 | 78.97 | 100.5 | 93.09 | 102.9 |
| Amfebutamone (Bupropion) | 87.88 | 68.96 | 80.34 | 108.8 | 97.53 | 84.27 | 79.56 | 110.2 | 92.31 | 88.44 | 77.45 | 102.7 |
| Loperamide hydrochloride | 41.61 | 36.25 | 72.53 | 75.46 | 24.22 | 47.5 | 35.74 | 31.75 | 31.99 | 34.26 | 51.45 | 40.91 |
| Mycophenolic (Mycophenolate) | 55.4 | 70.27 | 56.93 | 59.03 | 40.28 | 48.07 | 45.69 | 43.23 | 43.23 | 28.9 | 44.63 | 24.73 |
| Cloxacillin sodium (Cloxacap) | 130.8 | 103.7 | 101.6 | 106.9 | 105.9 | 80 | 69.13 | 70.4 | 69.87 | 110.7 | 116.6 | 106.1 |
| Amoxicillin sodium (Amox) | 127.2 | 98.11 | 103.4 | 101.8 | 101.8 | 88.13 | 71.08 | 66.94 | 65.21 | 115.9 | 115.1 | 98.18 |
| Tetracycline HCl | 104.5 | 93.11 | 88.07 | 104.5 | 81.94 | 96.69 | 77.67 | 79.25 | 53.3 | 82.79 | 100.5 | 99.91 |
| Vancomycin HCl (Vancocin) | 104.2 | 91.83 | 90.26 | 105.6 | 97.4 | 85.55 | 79.16 | 102 | 62.87 | 83.4 | 96.78 | 102.3 |
| Xylometazoline HCl | 116.1 | 90.08 | 96.3 | 102.5 | 92.29 | 82.83 | 72.93 | 76.43 | 60.23 | 101.9 | 116 | 100.4 |
| Phenacetin | 133.3 | 92.88 | 91.69 | 105.1 | 95.75 | 90.53 | 73.24 | 81.9 | 63.91 | 106.3 | 118.8 | 91.99 |

TABLE 4-continued

The results of antibiotic drug inhibiting cancer cell lines

| | | | | | | | | | | | |
|---|---|---|---|---|---|---|---|---|---|---|---|
| Trazodone hydrochloride (Desyrel) | 126 | 97.82 | 87.8 | 102.9 | 106.6 | 89.4 | 73.46 | 58.38 | 57.56 | 111.2 | 113.5 | 95.49 |
| Thiamphenicol (Thiophenicol) | 150.2 | 89.24 | 95.4 | 115.7 | 105.7 | 102.5 | 86.08 | 54.04 | 51.12 | 112 | 111.8 | 93.48 |
| Ciclopirox ethanolamine | 54.81 | 53.67 | 48.29 | 66.99 | 28.95 | 46.57 | 47.7 | 31.98 | 51.75 | 21.76 | 29.08 | 18.27 |
| Niclosamide (Niclocide) | 42.84 | 33.36 | 37.69 | 54.68 | 17.59 | 40.72 | 41.93 | 23.94 | 26.74 | 20.26 | 30.66 | 25.52 |
| Etravirine (TMC125) | 53.42 | 56.33 | 95.38 | 64.29 | 28.26 | 41.11 | 41.88 | 34.01 | 36.38 | 37.32 | 46.3 | 59.38 |
| Indacaterol Maleate | 100.3 | 72.48 | 102.6 | 79.3 | 95.33 | 85.38 | 91.37 | 61.71 | 62.58 | 87.23 | 82.13 | 82.57 |
| Pentamidine | 70.35 | 60.46 | 79 | 90.88 | 82.91 | 66.18 | 55.02 | 50.89 | 43.93 | 49.78 | 45.83 | 67.31 |
| Clofazimine | 105.9 | 74.24 | 102.4 | 97.28 | 65.06 | 76.57 | 72.2 | 75.16 | 80.57 | 81.2 | 72.91 | 82.51 |
| Azithromycin Dihydrate | 97.15 | 62.3 | 97.76 | 94.01 | 89.64 | 75.31 | 71.29 | 49.99 | 70.34 | 97.37 | 70.64 | 91.04 |
| Chlortetracycline HCl | 107.5 | 93.38 | 83.24 | 99.29 | 92.2 | 82.06 | 63.71 | 97.44 | 80.27 | 108 | 97.1 | 91.41 |
| Benzylpenicillin sodium | 105.8 | 86.92 | 94.7 | 110.4 | 111.9 | 101.4 | 95.32 | 66.96 | 71.55 | 112.6 | 97.68 | 93.15 |
| Chlorquinaldol | 66.42 | 30.18 | 65.02 | 78.08 | 40.07 | 62.79 | 53.91 | 20.58 | 32.44 | 35.48 | 42.95 | 41.77 |
| Primaquine Diphosphate | 65.67 | 50.72 | 65.44 | 60.19 | 54.76 | 66.47 | 49.82 | 59.86 | 59.63 | 38.67 | 35.93 | 81.46 |
| Colistimethate Sodium | 101.1 | 74.61 | 76.75 | 103.4 | 64.02 | 82.31 | 76.87 | 77.78 | 83.33 | 94.89 | 77.04 | 86.46 |
| Clofoctol | 110.3 | 83.02 | 102.1 | 97.78 | 73.11 | 78.69 | 65.81 | 73.17 | 74.92 | 108.6 | 94.57 | 105.4 |
| Rosuvastatin calcium (Crestor) | 95.68 | 85.86 | 90.19 | 102.2 | 80.39 | 80.17 | 65.52 | 93.28 | 101.7 | 105.1 | 103.5 | 92.53 |
| Mevastatin | 65.61 | 77.77 | 56.06 | 100.1 | 44.67 | 72.3 | 83.58 | 81.01 | 85.28 | 30.91 | 29.83 | 48 |

What is claimed is:

1. A method for treating a cancer comprising: administering to a subject in need thereof a pharmaceutical composition comprising a therapeutically effective amount of thonzonium bromide or a pharmaceutical acceptable salt thereof, wherein the cancer is selected form the group consisting of lung cancer, gastrointestinal tract cancer, colorectal cancer, kidney cancer, tongue squamous cell carcinoma, osteosarcoma, bladder cancer, cervical cancer, breast cancer, blood cancer, skin cancer, liver cancer, pancreatic cancer, ovarian cancer, and combination thereof.

* * * * *